US009694127B2

(12) United States Patent
Zink et al.

(10) Patent No.: US 9,694,127 B2
(45) Date of Patent: Jul. 4, 2017

(54) BIOREACTOR UNIT FOR USE IN BIOARTIFICIAL KIDNEY DEVICE

(71) Applicant: AGENCY FOR SCIENCE, TECHNOLOGY AND RESEARCH, Singapore (SG)

(72) Inventors: Daniele Zink, Singapore (SG); Yar Oo Zay, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 319 days.

(21) Appl. No.: 14/395,810

(22) PCT Filed: Apr. 22, 2013

(86) PCT No.: PCT/SG2013/000159
§ 371 (c)(1),
(2) Date: Oct. 20, 2014

(87) PCT Pub. No.: WO2013/158047
PCT Pub. Date: Oct. 24, 2013

(65) Prior Publication Data
US 2015/0076066 A1 Mar. 19, 2015

Related U.S. Application Data

(60) Provisional application No. 61/636,199, filed on Apr. 20, 2012.

(51) Int. Cl.
A61M 1/34 (2006.01)
B01D 63/02 (2006.01)

(52) U.S. Cl.
CPC ........ *A61M 1/3489* (2014.02); *A61M 1/3417* (2014.02); *A61M 1/3434* (2014.02); *A61M 1/3472* (2013.01); *B01D 63/02* (2013.01)

(58) Field of Classification Search
CPC .............. A61M 1/3417; A61M 1/3434; A61M 1/3472; A61M 1/3489; B01D 63/02
See application file for complete search history.

(56) References Cited

FOREIGN PATENT DOCUMENTS

EP          2 314 672 A2      4/2011
WO     WO 2011/040889 A1    4/2011

OTHER PUBLICATIONS

Aebischer, Patrick, et al., "Renal Epithelial Cells Grown on Semipermeable Hollow Fibers as a Potential Ultrafiltrate Processor", American Society for Artificial Internal Organs, vol. 33, No. 3, pp. 96-102, (1987).
Aebischer, Patrick, et al., "The Bioartificial kidney: Progress Towards an Ultrafiltration Device with Renal Epithelial Cells Processing", Life Support Systems, vol. 5, No. 2, pp. 159-163, (1987).

(Continued)

Primary Examiner — John Kim
(74) Attorney, Agent, or Firm — Blakely, Sokoloff, Taylor & Zafman LLP

(57) ABSTRACT

There is provided a bioreactor device having cells, including human primary proximal tubule cells (HPTCs) or HPTC-like cells on the exterior surface of hollow fiber membranes included within the device. Also provided are bioartificial kidney devices incorporate the bioreactor device and methods of using such devices.

20 Claims, 13 Drawing Sheets

(56) References Cited

OTHER PUBLICATIONS

Boswell, R.N., et al., "Interleukin 6 Production By Human Proximal Tubular Epithelial Cells In Vitro: Analysis of the Effects of Interleukin-1α (IL-1α) and Other Cytokines", Nephrology Dialysis Transplantation, vol. 9, No. 6, pp. 599-606, (1994).
Chertow, Glenn M., et al., "Toward the Promise of Renal Replacement Therapy", Journal of the American Society of Nephrology, vol. 19, No. 5, pp. 839-840, (2008).
Dong, Xinggang, et al., "Construction of Bioartificial Renal Tubule Assist Device in Vitro and its Function of Transporting Sodium and Glucose", J. Huazhong Univ. Sci. Technolog. Med. Sci., vol. 29, No. 4, pp. 517-521, (2009).
Fernandez-Real, Jose-Manuel, et al., "Circulating Interleukin 6 Levels, Blood Pressure, and Insulin Sensitivity in Apparently Healthy Men and Women", The Journal of Clinical Endocrinology & Metabolism, vol. 86, No. 3, pp. 1154-1159, (2001).
Fissell, William H., et al., "Bioartificial Kidney Alters Cytokine Response and Hemodynamics in Endotoxin-Challenged Uremic Animals", Blood Purification, vol. 20, No. 1, pp. 55-60, (2002).
Fissell, William H., et al., "Bioartificial Kidney Ameliorates Gram-Negative Bacteria-Induced Septic Shock in Uremic Animals", Journal of the American Society of Nephrology, vol. 14, No. 2, pp. 454-461, (2003).
Humes, H. David, et al., "Tissue Engineering of a Bioartificial Renal Tubule Assist Device: In Vitro Transport and Metabolic Characteristics", Kidney International, vol. 55, No. 6, pp. 2502-2514, (1999).
Humes, H. David, et al., "Repacement of Renal Function in Uremic Animals with a Tissue-Engineered Kidney", Nature Biotechnology, vol. 17, No. 5, pp. 451-455, (May 1999).
Humes, H. David, et al., "Metaboiic Replacement of Kidney Function in Uremia Animals with a Bioartificial Kidney Containing Human Cells", American Journal of Kidney Diseases, vol. 39, No. 5, pp. 1078-1087, (May 2002).
Humes, H. David, et al., "The Bioartificial Kidney in the Treatment of Acute Renal Failure", Kidney International, vol. 61, Supplement 60, pp. S121-S125, (2002).
Humes, H. David, et al., "Initial Ciinical Results of the Bioartificial Kidney containing Human Cells in ICU Patients with Acute Renal Failure", Kidney International. vol. 66, No. 4, pp. 1578-1586, (2004).
Inagaki, Miho, et al., "Prevention of LLC-PK: Cell Overgrowth in a Bioartificial Renal Tubule Device using a MEK Inhibitor: U0126", Journal of Biotechnology, vol. 132, No. 1, pp. 57-64, (2007).
Ip, Tze Kin, et al., "Cellular Control of Membrane Permeability—Implications for a Bioartificial Renal Tubule", Transactions—American Society for Artificial Internal Organs, vol. 34, No. 3, pp. 351-355, (1988).
Ip, Tze Kin, et al., "Renal Epithelial-Cell-Controlled Solute Transport Across Permeable Membranes as the Foundation for a Bioartificial Kidney", Artificial Organs, vol. 13, No. 1, pp. 58-65, (1989).
Li, Yao, et al., "Effects of Quantum Dots on Different Renal Proximal Tubule Cell Models and on Gel-Free Renal Tubules Generated In Vitro", Nanotoxicology, vol. 6, No. 2, pp. 121-133, (2012).
Mao, Huijuan, et al., "Effect of Continuous Bioartificial Kidney Therapy on Porcine Multiple Organ Dysfunction Syndrome with Acute Renal Failure", ASAIO Journal, vol. 53, No. 3, pp. 329-334, (2007).
Minuth, Will W., et al., "Renal Epithelia in Long Term Gradient Culture for Biomaterial Testing and Tissue Engineering", Biomedical Materials and Engineering, vol. 15, Nos. 1-2, pp. 51-61, (2005).
Minuth, Will W., et al., "Technical and Theoretical Considerations about Gradient Perfusion Culture for Epithelia used in Tissue Engineering, Biomaterial Testing and Pharmaceutical Research", Biomed. Mater., vol. 2, No. 2, pp. R1-R11, (2007).
Ni, Ming, et al., "Characterization of Membrane Materials and Membrane Coatings for Bioreactor Units of Bioartificial Kidneys", Biomaterials, vol. 32, No. 6, pp. 1465-1476, (2011).
Ni, Ming, et al., "The Use of a Library of Industrial Materials to Determine the Nature of Substrate-Dependent Performance of Primary Adherent Human Cells", Biomaterials, vol. 33, No. 2, pp. 353-364, (2011).
Oo, Zay Yar, et al., "The Performance of Primary Human Renal Cells in Hollow Fiber Bioreactors for Bioartificial Kidneys", Biomaterials, vol. 32, No. 34, pp. 8806-8615, (2011).
Oo, Zay Yar, et al., "A Novel Design of Bioartificial Kidneys with Improved Cell Performance and Haemocompatibility", J. Cell. Mol. Med., vol. 17, No. 4, pp. 497-507, (2013).
Ozgen, Nazira, et al., "Evaluation of Long-Term Transport Ability of a Bioartificial Renal Tubule Device using LLC-$PK_1$ Cells", Nephrology Dialysis Transplantation, vol. 19, No. 9, pp. 2198-2207, (2004).
Saito, Akira, "Research into the Development of a Wearable Bioartificial Kidney with a Continuous Hemofilter and a Bioartificial Tubule Device using Tubular Epithelial Cells", Artificial Organs, vol. 28, No. 1, pp. 58-63, (2004).
Saito, Akira, et al., "Present Status and Perspectives of Bioartificial Kidneys", Japanese Society for Artificial Organs, vol. 9, No. 3, pp. 130-135, (2006).
Saito, Akira, et al., "Present Status and Prespective of the Development of a Bioartificial Kidney for Chronic Renal Failure Patients", Therapeutic Apheresis and Dialysis, vol. 10, No. 4, pp. 342-347, (2006).
Saito, Akira, et al., "Present Status and Future Perspectives on the Development of Bioartificial Kidneys for the Treatment of Acute and Chronic Renal Failure Patients", Hemodialysis International, vol. 15, No. 2, pp. 183-192, (2011).
Saito, Akira, et al., "Evaluation of Bioartificial Renal Tubule Device Prepared with Lifespan-Extended Human Renal Proximal Tubular Epithelial Cells", Nephrology Dialysis Transplantation, vol. 27, No. 8, pp. 3091-3099, (2012).
Sanechika, Noriyuki, et al., "Development of Bioartificial Renal Tubule Devices with Lifespan-Extended Human Renal Proximal Tubular Epithelial Cells", Nephrology Dialysis Transplantation, vol. 26, No. 9, pp. 2761-2769, (2011).
Steensberg, Adam, et al., "IL-6 Enhances Plasma IL-1ra, IL-10, and Cortisol in Humans", Am. J. Physiol. Endocrinol. Metab., vol. 285, No. 2, pp. E433-E437, (2003).
Tasnim, Farah, et al., "Achievements and Challenges in Bioartificial Kidney Development", Fibrogenesis & Tissue Repair, vol. 3, No. 14, pp. 1-12, (2010).
Tasnim, Farah, et al., "Effects of Bone Morphogenetic Proteins on Primary Human Renal Cells and the Generation of Bone Morphogenetic Protein-7-Expressing Cells for Application in Bioartificial Kidneys", Tissue Engineering: Part A, vol. 18, Nos. 3-4, pp. 262-276, (2012).
Terashima Masuo, et al., "Evaluation of Water and Electrolyte Transport of Tubular Epithelial Cells under Osmotic and Hydraulic Pressure for Development of Bioartificial Tubules", Artificial Organs, vol. 25, No. 3, pp. 209-212, (2001).
Tsuruoka, Shuichi, et al., "Removal of Digoxin and Doxorubicin by Multidrug Resistance Protein-Overexpressed Cell Culture in Hollow Fiber", Kidney International, vol. 56, No, 1, pp. 154-163, (1999).
Tsuruoka, Shuichi, et al., "Specific Therapy of Digoxin Intoxication in Dogs by Hybrid Kidney Overexpressing Multidrug Resistance Protein", Kidney International, vol. 62, No. 4, pp. 1332-1337, (2002).
Tumlin, James, et al., "Efficacy and Safety of Renal Tubule Cell Therapy for Acute Renal Failure", J. Am. Soc. Nephrol., vol. 19, No. 5, pp. 1034-1040, (2008).
Ueda, Hideto, et al., "Asymmetrically Functional Surface Properties on Biocompatible Phospholipid Polymer Membrane for Bioartificial Kidney", J. Biomed. Mater. Res. A., vol. 77, No. 1, pp. 19-27, (2006).
Uludag, Hasan, et al., "Control of Water Flux in a Bioartificial Kidney", Transactions—American Society for Artificial Internal Organs, vol. 35, No. 3, pp. 523-527, (1989).

(56) References Cited

OTHER PUBLICATIONS

Uludag, Hasan, et al., "Transport Functions in a Bioartificial Kidney Under Uremic Conditions", The International Journal of Artificial Organs, vol. 13, No. 2, pp. 93-97, (1990).

Wang, Hengjin, et al., "Improvement of Cytokine Response and Survival Time by Bioartificial Kidney Therapy in Acute Uremic Pigs with Multi-Organ Dysfunction", Int. J. Artif. Organs, vol. 33, No. 8, pp. 526-534, (2010).

Zhang, Huishi, et al., "Generation of Easily Accessible Human Kidney Tubules on Two-Dimensional Surfaces In Vitro", J. Cell. Mol. Med., vol. 15, No. 6, pp. 1297-1298, (2011).

PCT Notification of Transmittal of the International Search Report and the Written Opinion of the International Searching Authority, or the Declaration for corresponding PCT Application No. PCT/SG2013/000159, 10 pp., (Jun. 18, 2013).

PCT Notification Concerning Transmittal of International Preliminary Report on Patentability (Chapter I of the Patent Cooperation Treaty) for corresponding PCT Application No. PCT/SG2013/000159, 7 pp., (Oct. 30, 2014).

Supplementary Examination Written Opinion received from the Intellectual Property Office of Singapore in corresponding Singapore Patent Application No. 11201406620Q, 4 pp., (Aug. 28, 2015).

Tsuruoka, Shuichi, et al., "Treatment of Digoxin Intoxication Model by Hybrid-Kidney with Hollowfibre Module for Clinical Haemodialysis", Nephrol. Dial. Transplant., vol. 19, No. 5. pp. 1339-1340, (2004).

US 9,694,127 B2

BIOREACTOR UNIT FOR USE IN BIOARTIFICIAL KIDNEY DEVICE

CROSS-REFERENCE TO RELATED APPLICATIONS

This patent application is a U.S. National Phase Application under 35 U.S.C. §371 of International Application No. PCT/SG2013/000159, filed on Apr. 22, 2013, which claims benefit of, and priority from, U.S. provisional application No. 61/636,199, filed on Apr. 20, 2012, the contents of which are hereby incorporated by reference.

FIELD OF THE INVENTION

The present invention relates to bioartificial kidney devices, and in particular to bioreactor units for inclusion in bioartificial kidney devices.

BACKGROUND OF THE INVENTION

Bioartificial kidneys (BAKs) have been contemplated in order to assist with, or as an alternative to, dialysis, hemofiltration or related blood purification methods. Aebischer and colleagues were the first to propose BAKs, comprising a hemofilter in series with two bioreactor units [27, 33, 34]. It was proposed by these authors that the hemofilter should be in series with 2 bioreactor units and that all three units contained in the BAK would be cartridges containing hollow fiber membranes (HFMs). The hemofilter was to be included to generate hemofiltrate with the blood flowing through the lumina of the HFM, while the bioreactors would contain Madin-Darby canine kidney (MDCK) cells or Lewis lung cancer-porcine kidney 1 (LLC-PK1) cells. Aebischer and colleagues did not construct the proposed BAKs, but did preliminary in vitro studies using membranes and HFMs [27, 33-37].

More recently, work done by Saito et al. [24, 25, 38-41], Humes et al. [1-4, 8, 9], Mao et al. [5] and Wang et al. [6] involves BAKs that contain a hemofilter in series with a single bioreactor having renal proximal tubule cells growing inside the lumen of the HFMs. The hemofiltrate flows through the lumen of the HFMs of the bioreactor, with blood flowing on the exterior side of the HFMs.

In particular, animal studies [1-7] and clinical trials [8, 9] were performed with these two-cartridge BAKs. Thus, with this arrangement, the hemofiltrate (which may also be referred to as ultrafiltrate) flows past the cells in the bioreactor, while the blood is separated from the cells by the semipermeable membrane of the HFMs, mimicking the architecture of the renal proximal tubule. It was expected that the bioreactor unit would replace or simulate functions of the renal proximal tubule. However, in a phase I/II clinical trial, no clear indication was obtained that proximal tubular-specific functions were contributed by the renal cells [8, 10].

Improved long-term survival in the group of patients that received BAK treatment was observed in a phase II clinical trial involving critically ill patients with acute kidney injury (AKI) [9]; the reasons for this clinical improvement remain unclear [10, 11]. Cytokine levels in serum and plasma were measured in various animal studies and the Phase I/II clinical trial [1, 2, 5-8]. Some changes in cytokine levels suggested that beneficial effects of BAK treatment might be a result of immunomodulatory functions [1, 2, 5-8]. However, the release of cytokines or other immunomodulators from the bioreactor unit has not been investigated, so far. A Phase II b clinical trial failed in 2006 (discussed in [9]), and since then no further clinical trials with BAK have been performed.

SUMMARY OF THE INVENTION

Previously designed BAKs can produce transmembrane pressure across the hollow fiber membranes in the bioreactor, which may damage renal epithelial cells. As well, the blood flows past the exterior surface of the hollow fiber membranes, which has not been optimized for hemocompatibility. This exterior surface is typically designed to be microporous and rough, and contact between the blood and the exterior HFM surface can lead to increased platelet adhesion, membrane clogging and thrombus formation.

The present invention relates to an alternative BAK design that incorporates a novel bioreactor device. In the described bioreactor, cells, including human primary proximal tubule cells (HPTCs), or HPTC-like cells derived from stem cells such as embryonic or induced pluripotent stem cells (iPSCs), are grown on the exterior surface of the hollow fiber membranes. Such an arrangement allows for blood to flow past the hemocompatible luminal surface of the hollow fiber membranes. The exterior surface of the hollow fiber membranes may be rough textured and may exhibit improved cytocompatibility compared to the typically smooth hemocompatible interior surface and may not require any modification or coating to support cell.

In one aspect, the invention provides a bioreactor device comprising: a housing having a blood inlet port; a blood outlet port; an hemofiltrate inlet port; and an hemofiltrate outlet port; one or more porous hollow fiber membranes contained within the housing, each of the one or more hollow fiber membranes being in fluid communication with the blood inlet port and the blood outlet port, and each of the one or more hollow fiber membranes comprising a hemocompatible luminal surface and a cytocompatible exterior surface that is cytocompatible for human primary renal proximal tubule cells (HPTCs) or stem cell-derived HPTC-like cells, each of the cytocompatible exterior surfaces covered with a confluent layer of the HPTCs or stem cell-derived HPTC-like cells, and being in fluid communication with the hemofiltrate inlet port and the hemofiltrate outlet port.

The confluent layer of HPTCs or stem-cell derived HPTC-like cells may comprise a differentiated single layer epithelium in which the paracellular spaces are sealed by tight junctions.

The HPTCs or stem-cell derived HPTC-like cells may be grown directly onto each of the cytocompatible exterior surfaces, each of the cytocompatible exterior surfaces being free from an additional coating, for example collagen IV or laminin.

Each of the cytocompatible exterior surfaces may have a rough texture relative to the hemocompatible luminal surface. Each of the cytocompatible exterior surfaces may be non-hemocompatible. Each of the cytocompatible exterior surfaces may have large pores relative to pores on the hemocompatible luminal surface, for example pores in the micrometer range.

The cytocompatible exterior surface may comprise one or more of polysulfone, polyethersulfone, polyarylethersulfone, polycarbonate, polyacrylonitirle, polyethylene, polyolefin, polypropylene and polyviylidene fluoride, ethylene vinyl alcohol copolymer, polymethylmethacrylate, polyamide and polyacrylate, optionally blended with a hydrophilic polymer, for example polyviylpyrrolidone or polyurethane.

Each of the hemocompatible luminal surfaces may comprises a smooth surface. Each of the hemocompatible luminal surfaces may have pores sized to allow for rapid fluid exchange but sized to exclude serum albumin. Each of the hemocompatible luminal surfaces may have pores in the sub-micron range.

The bioreactor device may comprise at least two of the hollow fiber membranes that are packed in the bioreactor device at a density less than the density of hollow fiber membranes in a commercial hemodialysis cartridge, for example a Gambro PrismafleX HF20 polyarylethersulfone hemodialysis cartridge or a Fresenius HF80S polysulfone hemodialysis cartridge.

In another aspect, the invention provides a bioartificial kidney device comprising: (i) a hemofiltration device comprising: a housing with a blood inlet port and a blood outlet port; one or more semi-permeable hollow fiber membranes contained within the housing, each of the one or more hollow fiber membranes being in fluid communication with the blood inlet port and the blood outlet port, and each of the one or more hollow fiber membranes comprising a hemocompatible luminal surface and an exterior surface, each of the exterior surfaces being in fluid communication with an hemofiltrate outlet port; and (ii) a bioreactor device as defined herein, the blood inlet port of the bioreactor device being in fluid connection with the blood outlet port of the hemofiltration device, and the hemofiltrate inlet port of the bioreactor being in fluid communication with the hemofiltrate outlet port of the hemofiltration device.

The bioartificial kidney may further comprise a first fluid line for connecting to a bloodstream of a subject, the first fluid line being in fluid communication with the blood inlet port of the hemofiltration device; a first pump for controlling blood flow rate from the subject; a first reservoir for holding hemofiltrate, the first reservoir in fluid communication with the hemofiltrate outlet port of the hemofiltration device and in fluid communication with the hemofiltrate inlet port of the bioreactor device; a second pump for controlling flow rate from the first reservoir; a second fluid line in fluid communication with the blood outlet port of the hemofiltrate device and in fluid communication with the blood inlet port of the bioreactor device; a third fluid line in fluid communication with the second fluid line and in fluid communication with the subject, the third fluid line connected to the second fluid line at a branch point; a three way connector at the branch point for controlling the amount of blood flowing from the blood outlet port of the hemofiltration device to the blood inlet port of the bioreactor device and for optionally diverting at least a portion of the blood into the third fluid line; a fourth fluid line in fluid communication with the blood outlet port of the bioreactor device and in fluid communication with the third fluid line; a third pump for controlling blood flow into the blood inlet port of the bioreactor device; a second reservoir for holding replacement fluid, the second reservoir being in fluid communication either with the blood inlet port of the hemofiltration device or with the third fluid line; and a fourth pump for controlling flow rate from the second reservoir.

The bioartificial kidney may further comprising a fifth pump for controlling blood flow rate from the third line into the subject, and may further comprise a third reservoir for collecting waste from the bioreactor device, the third reservoir in fluid communication with the hemofiltrate outlet port of the bioreactor device.

The third reservoir may also be in fluid communication with the first reservoir. The bioartificial kidney device may further comprise a sixth pump for controlling flow rate from the third reservoir to the first reservoir.

The hemofiltration device may be a high flux hemofiltration cartridge, including for example a high flux pediatric hemofiltration cartridge. The bioreactor device may have a smaller volume than the hemofiltration device.

In another aspect, the invention provides a method of providing renal function to a subject comprising: connecting the bioartificial kidney device of the invention to a subject in need of renal replacement therapy. The method may provide blood hemofiltration to the subject.

The subject may be any subject in need of provision of renal function, including a human or a non-human animal.

In the method, connecting may comprise connecting the bioartificial kidney device of the invention to the subject via the first fluid line and the third fluid line so that blood flows from the subject into the first fluid line, through the bioartificial kidney device and into the subject via the third fluid line.

The first pump may control blood flow from the subject into the blood inlet port of the hemofiltration device at a flow rate of from about 100 ml/min to about 200 ml/min, and the second pump may control hemofiltrate flow from the first reservoir into the hemofiltrate inlet port of the bioreactor device at a flow rate of from about 10 ml/min to about 100 ml/min, or from about 10 ml/min to about 30 ml/min. The third pump may control blood flow into the blood inlet port of the bioreactor device at a flow rate of from about 10 ml/min to about 100 ml/min, or from about 10 ml/min to about 30 ml/min.

Other aspects and features of the present invention will become apparent to those of ordinary skill in the art upon review of the following description of specific embodiments of the invention in conjunction with the accompanying figures.

BRIEF DESCRIPTION OF THE DRAWINGS

The figures, which illustrate, by way of example only, embodiments of the present invention, are as follows.

FIG. 5. BAK design. The blood flows from the animal or patient (red, bloodline: red) at a flow rate of 100-200 ml/min into the hemofilter (1), which consists of a normal hemodialysis/hemofiltration cartridge. The drawing illustrates the pre-dilution mode and pumps are symbolized by circles. The extra-HFM space containing the hemofiltrate and the hemofiltrate reservoir are depicted in blue. The blood outlet port of the hemofilter is linked to a 3-way connector and most of the blood flows back to the animal/patient. The remaining blood and the hemofiltrate are pumped at similar flow rates of approximately 10-30 ml/min. into the bioreactor (2). HPTC (green) grow in the bioreactor on the outer surfaces of the HFM, where they are exposed to the hemofiltrate. The blood flows in the lumina of the HFM. This configuration is shown enlarged in the upper right. The processed hemofiltrate exiting the bioreactor is depicted in yellow (waste).

DETAILED DESCRIPTION

There is presently provided a bioreactor device for inclusion in a bioartificial kidney. The bioreactor device is designed using an arrangement that is reversed from the bioreactors that are currently used in BAKs and which have been used for more than a decade [1-10, 24-26]. That is, in the bioreactor device as described herein, cells, including for example human primary renal proximal tubule cells (HPTCs), are grown on the exterior surfaces of hollow fiber membranes (HFMs). The bioreactor device is designed so that hemofiltrate will flow in the extra-luminal space surrounding the HFMs, past the cells which are present on the exterior surface of the HFMs. The blood that is to be treated is flowed through the lumens of the HFMs, and thus contacts the hemocompatible surfaces that line the lumens. Such an arrangement may avoid problems seen with HFMs in other bioreactors, including clogging of the pores with blood components [12]. As well, the bioreactor device as described herein may exhibit improved hemocompatibility. Furthermore, application of the cells to the exterior surface may avoid modification or coating of the exterior surface, and thus allows for use of unmodified commercially available HFM in the bioreactor device.

It will be appreciated that reference to hemofiltrate or hemofiltration may also be referred to in the art as ultrafiltrate and ultrafiltration, or even as filtrate or filtration.

Figure 1:
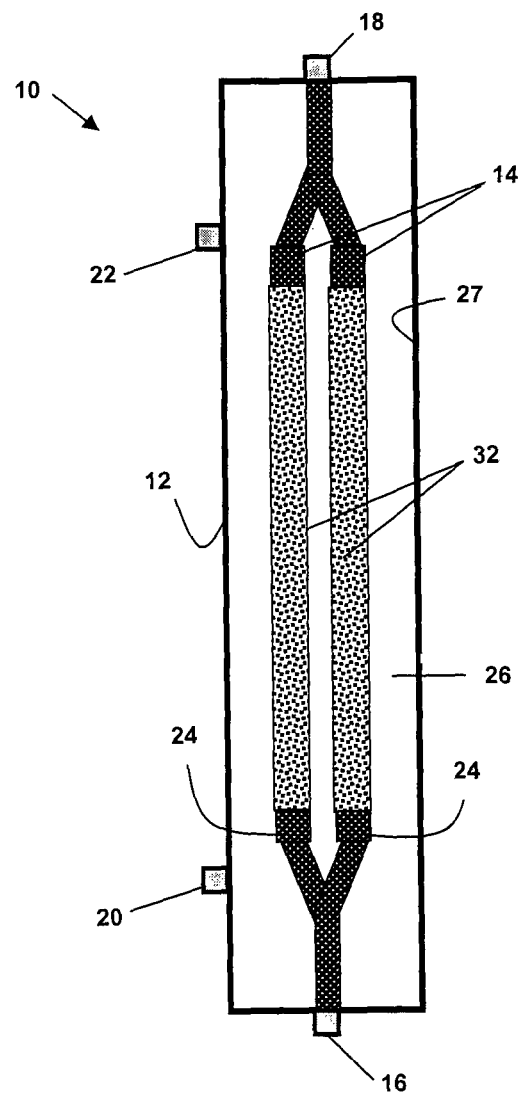
FIG. 1 illustrates an embodiment of the bioreactor device of the invention.

Thus, there is presently provided a bioreactor device 10, as depicted in FIG. 1.

Figure 2:
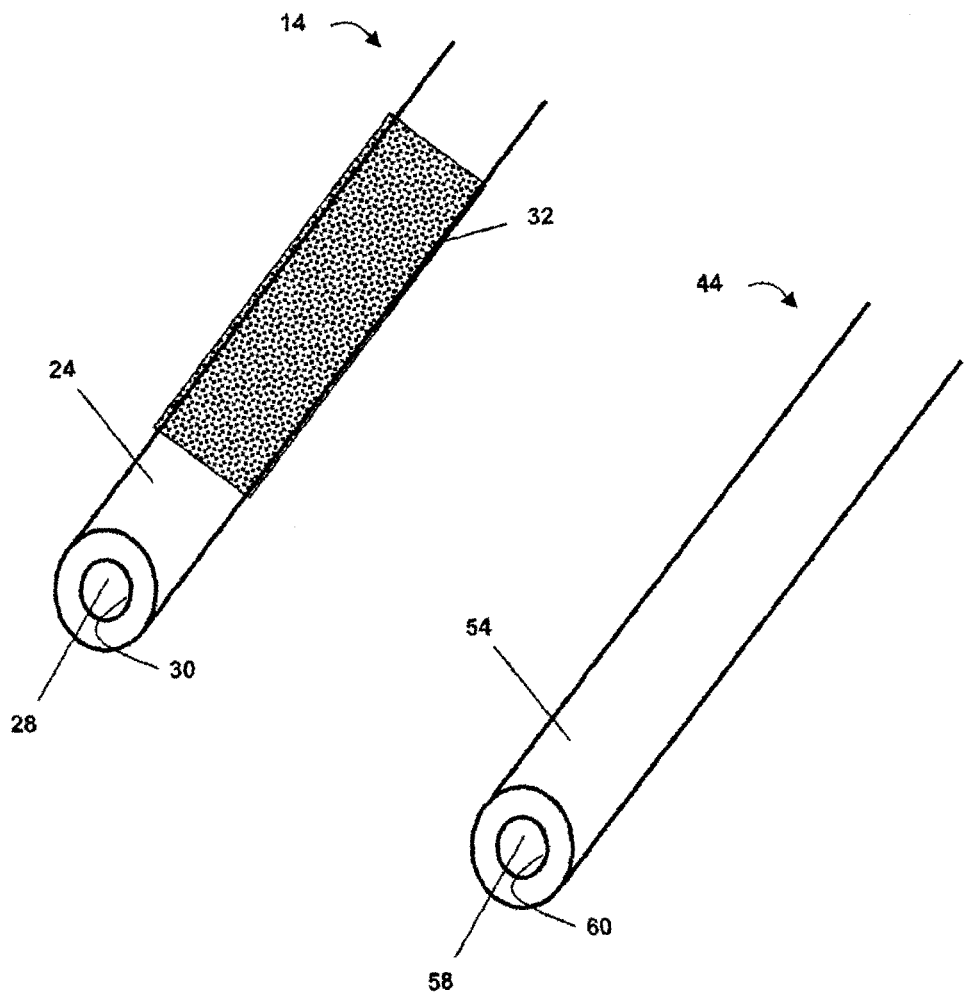
FIG. 2 illustrates an embodiment of hollow fiber membranes included in the bioreactor device of the invention with a cell layer (left) or in the hemofiltration device of the invention without a cell layer (right).

The bioreactor device 10 comprises a housing 12. Housing 12 contains one or more hollow fiber membranes 14 (FIGS. 1 and 2).

Housing 12 also has a blood inlet port 16 and blood outlet port 18, to allow blood to flow into and out of bioreactor device 10. Inlet port 16 is in fluid communication with each of one or more hollow fiber membranes 14. Similarly, the one or more hollow fiber membranes 14 are each in fluid communication with blood outlet port 18, thus creating a blood flow path through the bioreactor device 10, from blood inlet port 16, through each of one or more hollow fiber membranes 14 and exiting via blood outlet port 18.

Housing 12 also has an hemofiltrate inlet port 20 and an hemofiltrate outlet port 22, to allow for flow of hemofiltrate into and out of the bioreactor device 10. Hemofiltrate inlet port 20 is in fluid communication with the exterior surface 24 of each of one or more hollow fiber membranes 14. Similarly, hemofiltrate outlet port 22 is also in fluid communication with the exterior surface of each of one or more hollow fiber membranes 14. Thus, there is a space 26 defined within the housing between the interior surface 27 of the housing 12 and the exterior surface 24 of each of one or more hollow fiber membranes 14, and there is an hemofiltrate flow path through the bioreactor device 10, from hemofiltrate inlet port 20, passed the exterior surfaces 24 of each of one or more hollow fiber membranes 14, exiting via hemofiltrate outlet port 22.

Thus, as indicated above, each hollow fiber membrane 14 has an exterior surface 24 and an interior lumen 28 defined by interior luminal surface 30.

Exterior surface 24 is cytocompatible, meaning that the surface is biologically, chemically and physically compatible with the growth and function of cells thereon. That is, the surface material from which exterior surface 24 is formed, as well as the topography or texture of exterior surface 24, should allow for adhesion, survival and growth of the cells and the formation of an epithelium and the performance of differentiated cellular function of the particular type of cell that is to be grown on the surface.

Exterior surface 24 may have a rough texture, which texture may contribute to the cytocompatibility of exterior surface 24. That is, exterior surface 24 may have a surface having an increased texture or roughness when compared with the texture of interior luminal surface 30. Such rough texture of exterior surface 24 may result in exterior surface 24 being non-hemocompatible, or at least less hemocompatible than interior luminal surface 30, as described below.

Exterior surface 24 of each hollow fiber membrane 14 may be porous. If present, the pores may be larger than any pores that may be present in the interior luminal surface 30. For example, exterior surface 24 may have pores in the micrometer range, meaning the pores are at least 1 micrometer in diameter, or may be from about 1 micrometer to about 10 micrometers in diameter or from about 1 micrometer to about 100 micrometers in diameter.

Due to the cytocompatibility of exterior surface 24, it may not be necessary to further modify or coat exterior surface 24. That is, in previously described bioreactor units, surfaces that are used as cell growth supports in the bioreactor have often been modified or coated with a cytocompatible coating, for example collagen IV, laminin, or attachin in order to encourage cell growth. Thus, in the presently described bioreactor device 10, exterior surface 24 may be free from any additional coating.

Thus, exterior surface 24 may formed from any cytocompatible material. Typically, exterior surface 24 will be formed from a polymer, including for example one or more of polysulfone, polyethersulfone, polyarylethersulfone, polycarbonate, polyacrylonitrile, polyethylene, polyolefin, polypropylene, polyviylidene fluoride, polypropylene and polyviylidene fluoride copolymer, ethylene vinyl alcohol copolymer, polymethylmethacrylate, polyamide, polyacrylate, polyamide and polyacrylate copolymer, any of which may be optionally blended with a hydrophilic polymer, for example polyviylpyrrolidone or polyurethane.

In contrast to exterior surface 24, interior luminal surface 30 is hemocompatible, meaning that the surface is biologically, chemically and physically compatible with blood. That is, the surface material from which interior luminal surface 30 is formed is not toxic or hemolytic, including chemically or physically, and allows for the flow of blood past the surface without adhering to the surface or damaging the blood components including blood cells.

Interior luminal surface 30 may have a smooth texture, which texture may contribute to the hemocompatibility of interior luminal surface 30. That is, interior luminal surface 30 may have a surface having a decreased texture or roughness when compared with the texture of exterior surface 24. Such smooth texture of interior luminal surface 30 may result in interior luminal surface 30 being non-cytocompatible, or at least less cytocompatible than exterior surface 24, as described below.

Interior luminal surface 30 of each hollow fiber membrane 14 may also be porous. If present, the pores may be smaller than any pores that may be present on the exterior surface 24. For example, interior luminal surface 30 may have pores in the submicrometer range, meaning the pores are less than 1 micrometer in diameter, and may be from about 0.001 micrometer to about 0.9 micrometers. Pores in interior luminal surface 30 may be sized to allow for rapid fluid exchange but still to exclude serum albumin, for example pores having a molecular weight cutoff in the range of about 35 kDa to about 50 kDa. For example, interior luminal surface 30 may have pores in the nanometer range, meaning the pores are at least 1 nanometer in diameter, or may be from about 1 nanometer to about 100 nanometers in diameter or from about 1 nanometer to about 900 nanometers in diameter.

In bioreactor device 10, exterior surface 24 of each hollow fiber membrane 14 is covered with a cell layer 32. The cells forming cell layer 32 may be human primary renal proximal tubule cells (HPTCs), or HPTC-like cells derived from stem cells including human stem cells, such as embryonic stem cells, induced pluripotent stem cells, mesenchymal stem cells or amniotic fluid-derived stem cells.

Each of primary renal proximal tubule cells, stem cell-derived HPTC-like cells, embryonic stem cells, induced pluripotent stem cells, mesenchymal stem cells and amniotic fluid-derived stem cells, are known. Human primary renal proximal tubule cells (HPTCs) are primary cells, which may be explanted from a human kidney, and which may be further cultured prior to assembly in bioreactor device 10. Stem cell-derived HPTC-like cells are cells that originate from stem cells, for example from embryonic stem cells, induced pluripotent stem cells, mesenchymal stem cells or amniotic fluid-derived stem cells, and which have been differentiated or at least partially differentiated to form cells having properties similar to proximal tubule cells. Induced pluripotent stem cells are cells that are derived from adult differentiated or partially differentiated cells and that have been treated to induce a pluripotent state. Induced pluripotent stem cells may then be differentiated into HPTC-like cells.

To increase biocompatibility of bioreactor 10 for use in a clinical setting, the cells that form cell layer 32 may be human cells.

Cell layer 32 is a confluent layer of cells, meaning that the cells in cell layer 32 so that adjacent cells touch each other and form a cover over exterior surface 24, or over at least a portion of exterior surface 24, without significant holes or gaps in the cover or between cells. For example, cell layer 32 may comprise a differentiated single layer epithelium in which the paracellular spaces are sealed by tight junctions.

As indicated above, exterior surface 24 may be cytocompatible in a manner that does not require any further coating or modification in order for cells that form cell layer 32 to adhere and grow on exterior surface 24. In order to form cell layer 32, cells of the desired cell type may be seeded onto exterior surface 24 and grown in suitable medium for a period of time and under suitable conditions for the seeded cells to divide and multiple to form a confluent layer over the desired region of exterior surface 24. This may be done prior or subsequent to assembly of the one or more hollow fiber membranes 14 into housing 12.

In some embodiments, bioreactor device 10 comprises at least two of hollow fiber membrane 14, which are packed into the housing 12 as described above and below. In some embodiments, bioreactor device 10 comprises a plurality of hollow fiber membrane 14, which are packed into the housing 12 as described above and below.

The density of packing of hollow fiber membrane 14 into housing 12 can influence the performance of bioreactor device 10. That is, when packed too tightly, growth of seeded cells to form the monolayer may be impaired, which may result in an incomplete cell layer 32, particularly when human cells are used. Thus, the hollow fiber membrane 14 may be included in housing 12 at a density that does not interfere with formation of cell layer 32. Such a density may vary depending on the particular cell type, growth medium and growth conditions used. A skilled person may readily determine a suitable density using routine laboratory methods. For example, hollow fiber membrane 14 may be packed in housing 12 at a density of about 500 HFMs/cm$^2$ or less, about 400 HFMs/cm$^2$ or less, about 300 HFMs/cm$^2$ or less, about 200 HFMs/cm$^2$ or less, or about 100 HFMs/cm$^2$ or less. For example, hollow fiber membrane 14 may be packed in housing 12 at a density of about 50 HFMs/cm$^2$ to about 500 HFMs/cm$^2$, or about 100 HFMs/cm$^2$ to about 200 HFMs/cm$^2$. In some embodiments, hollow fiber membrane 14 may be packed in housing 12 at a density about or less than the density found in commercially available hemodialysis cartridges, including for example a Gambro PrismafleX™ HF20 polyarylethersulfone hemodialysis cartridge or a Fresenius HF80S polysulfone hemodialysis cartridge.

Thus, the bioreactor device as described herein comprises a cell layer on the exterior, cytocompatible rough surface of the hollow fiber membranes contained within the device. When human cells are used, such cells are often more difficult to grow in culture, and may be more sensitive to growth conditions including the topography and material of the support surface, when compared to cultured animal cells. For instance, animal cell lines used by Ip and Aebischer [27] are indeed much less selective than HPTC in terms of growth substrates [10], and thus would make no difference on which kind of surface these animal cells are grown. In other studies performed with a rabbit cell line, a collagen coating was applied to the outer HFM surfaces [29, 30].

In contrast, it now appears that human cells, including HPTCs, may perform better on the rough exterior surface of HFMs than on the smooth, hemocompatible intraluminal layer. An obvious difference between these distinct surfaces is their topology, which could impact cell performance. Without being limited by theory, the influence of surface topology may be indirect, mediated by increased protein adsorption to the rough surface [12]. Indeed, a hallmark of hemocompatible surfaces is their reduced adhesiveness for proteins and cells. Previous studies showed that HPTC perform particularly well on adhesive substrates like DOPA-coated surfaces or membranes consisting of PSF-Fullcure [13]. Notably, the hemocompatibility of such surfaces, which sustain HPTC performance, is very low with extensive platelet adhesion and activation. Thus, as demonstrated herein, cytocompatible surfaces may be non-hemocompatible, and vice versa. Bioreactor devices having the arrangement as described herein would not mimic the architecture of the renal tubule.

With the presently described bioreactor device, human cells, including HPTCs may be able to form differentiated epithelia even on uncoated exterior surfaces of HFMs, and such epithelia may express characteristic marker proteins and brush border enzymes, and may remain confluent and well differentiated when exposed to human hemofiltrate at relevant flow rates. Such functional epithelia may demonstrate baso-lateral uptake and transport from the blood compartment into the waste compartment, and may prevent back-leak of waste products such as urea and creatinine into the blood compartment.

The use of uncoated, unmodified HFMs may therefore be less costly and reduce batch-to-batch variability, in particular when compared to approaches where extracellular matrix proteins derived for natural sources are used [1, 4, 8, 9]. The performance of the cell layer in the bioreactor device may therefore be more reliable when a cytocompatible material is used that does not require further modifications to achieve cell growth, survival and differentiation.

Another advantage of placing the cell layer on the exterior surfaces of HFMs is that cell performance can be readily monitored. No sectioning of the tiny HFM is required for visual monitoring and large numbers of HFM can be rapidly assessed. Furthermore, cell seeding is greatly facilitated and sheer stress during injection of the cells into the narrow HFM lumen is avoided; cells such as HPTC are particularly sensitive to mechanical stress.

The bioreactor device may be incorporated into a bioartifical kidney (BAKs). BAKs typically include a hemofiltration unit serially connected to at least one bioreactor unit, such that blood from the patient is first processed by the hemofiltration unit, and then filtrate or blood from the patient is then further processed by the bioreactor unit.

Thus, in another aspect, there is provided a bioartificial kidney device that comprises the bioreactor device as described herein.

Figure 3:
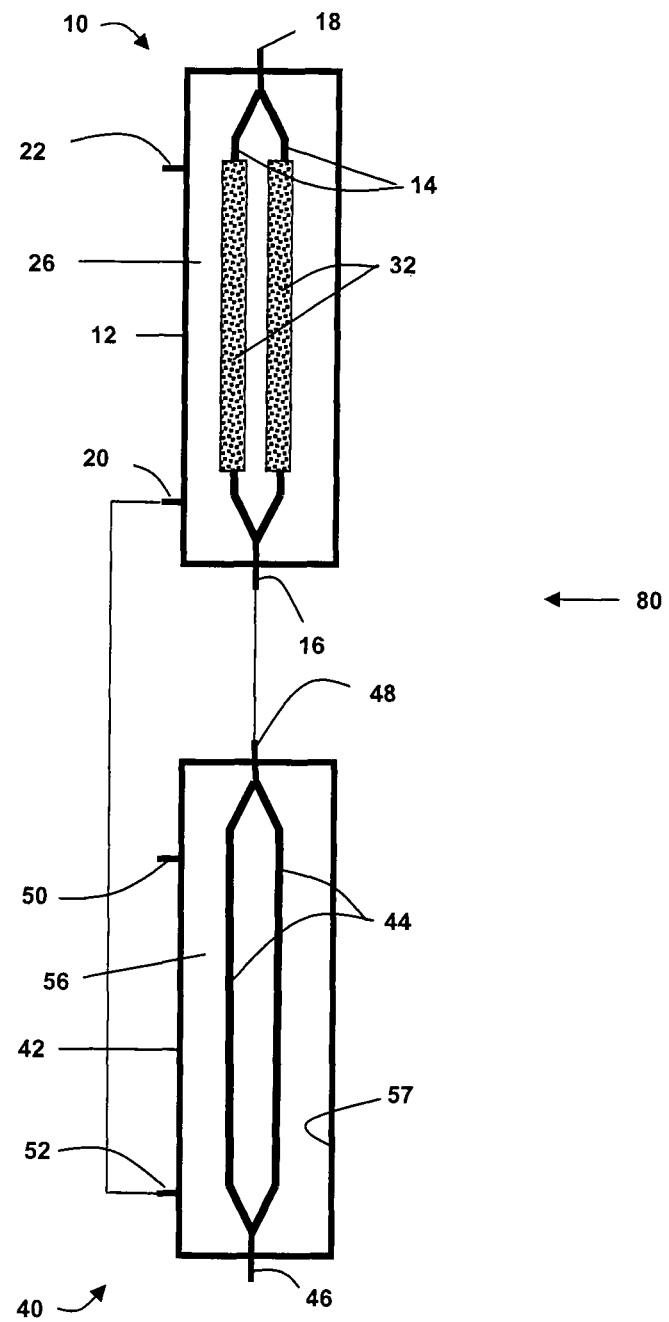
FIGS. 3 and 4 illustrate various embodiments of the bioartificial kidney device of the invention.

As depicted in FIG. 3, bioartificial kidney device 80 comprises hemofiltration device 40 connected to bioreactor 10. hemofiltration devices are commercially available.

Hemofiltration device 40 includes housing 42. Housing 42 contains one or more hollow fiber membranes 44. Each of hollow fiber membrane 44 is semi-permeable (porous), and may be constructed from the same material as described for the hollow fiber membranes 14 in bioreactor device 10, above. Thus, each hollow fiber membrane 44 has an exterior surface 54 and an interior lumen 58 defined by interior luminal surface 60. Interior luminal surface 60 is hemocompatible and may have a smooth texture.

Hemofiltration device 40 has a blood inlet port 46 and blood outlet port 48. Blood inlet port 46 is in fluid communication with each of one or more hollow fiber membranes 44. Similarly, the one or more hollow fiber membranes 44 are each in fluid communication with blood outlet port 48, thus creating a blood flow path through the hemofiltration device 40, from blood inlet port 46, through lumen 58 of each of one or more hollow fiber membranes 44 and exiting via blood outlet port 48.

The semi-permeable membrane that forms each hollow fiber membrane 44 allows for passage of solutes in blood from interior lumen 58 to the space 56 between interior surface 57 of housing 42 and the exterior surface 54 of each hollow fiber membrane 44.

Housing 42 may optionally have filtrate solution inlet port 50. If present, filtrate solution inlet port 50 may optionally be in fluid communication with the exterior surface 54 of each of one or more hollow fiber membranes 44. However, typically filtrate solution inlet port 50 is not required and is not used in hemofiltration device 40.

Housing 42 possesses an hemofiltrate outlet port 52, to allow for flow of hemofiltrate out of the hemofiltration device 40. Hemofiltrate outlet port 52 is in fluid communication with the exterior surface 54 of each of one or more hollow fiber membranes 44. Thus, hemofiltrate flow path from exterior surfaces 54 of each of one or more hollow fiber membranes 44, through space 56 exiting via hemofiltrate outlet port 52.

In bioartificial kidney device 80, hemofiltration device 40 is connected to bioreactor device 10. The blood inlet port 16 of bioreactor device 10 is in fluid communication with blood outlet port 48 of hemofiltration device 40. Similarly, hemofiltrate inlet port 20 of the bioreactor 10 is in fluid communication with the hemofiltrate outlet port 52 of the hemofiltration device 40. For example, the blood inlet port 16 may be connected to blood outlet port 48 and the hemofiltrate inlet port 20 may be connected to hemofiltrate outlet port 52 by a fluid line such as tubing.

The above description of bioartificial kidney device 80 describes the basic device. Thus, as blood flows into bioartificial kidney device 80, the blood will first enter hemofiltration device 40. Blood flows in blood inlet port 46, through interior lumen 58 of each hollow fiber membrane 44, and then out through blood outlet port 48. While blood is flowing through the interior lumen 58 of each hollow fiber membrane 44 within hemofiltration device 40, solutes in the blood may pass through the semi-permeable walls of hollow fiber membrane 44 into space 56 and then eventually out hemofiltrate outlet port 52, thus exiting hemofiltration device 40.

At least some of the blood exiting hemofiltration device 40 may then flow into bioreactor device 10 via blood inlet port 16, through interior lumen 28 of each hollow fiber membrane 14, and then out through blood outlet port 18.

While blood is flowing through the interior lumen 28 of each hollow fiber membrane 14 within bioreactor device 10, cells within cell layer 32 may transport solutes from interior lumen 28 and out into space 26 into the hemofiltrate flowing through space 26. Thus, in addition to blood, hemofiltrate may flow from hemofiltrate outlet port 52 of hemofiltration device 40 into bioreactor device 10 via hemofiltrate inlet port 20. Hemofiltrate will flow through space 26, past cell layers 32, and then exit bioreactor device via hemofiltrate outlet port 22. It will be appreciated that some components from the hemofiltrate, for example sugars, amino acids, may be reabsorbed by cell layer 32 back into the blood.

For ease of use, the bioartificial kidney device may further include various fluid lines, pumps and reservoirs to control and direct the flow of blood and hemofiltrate while the BAK is in use.

Figure 4:
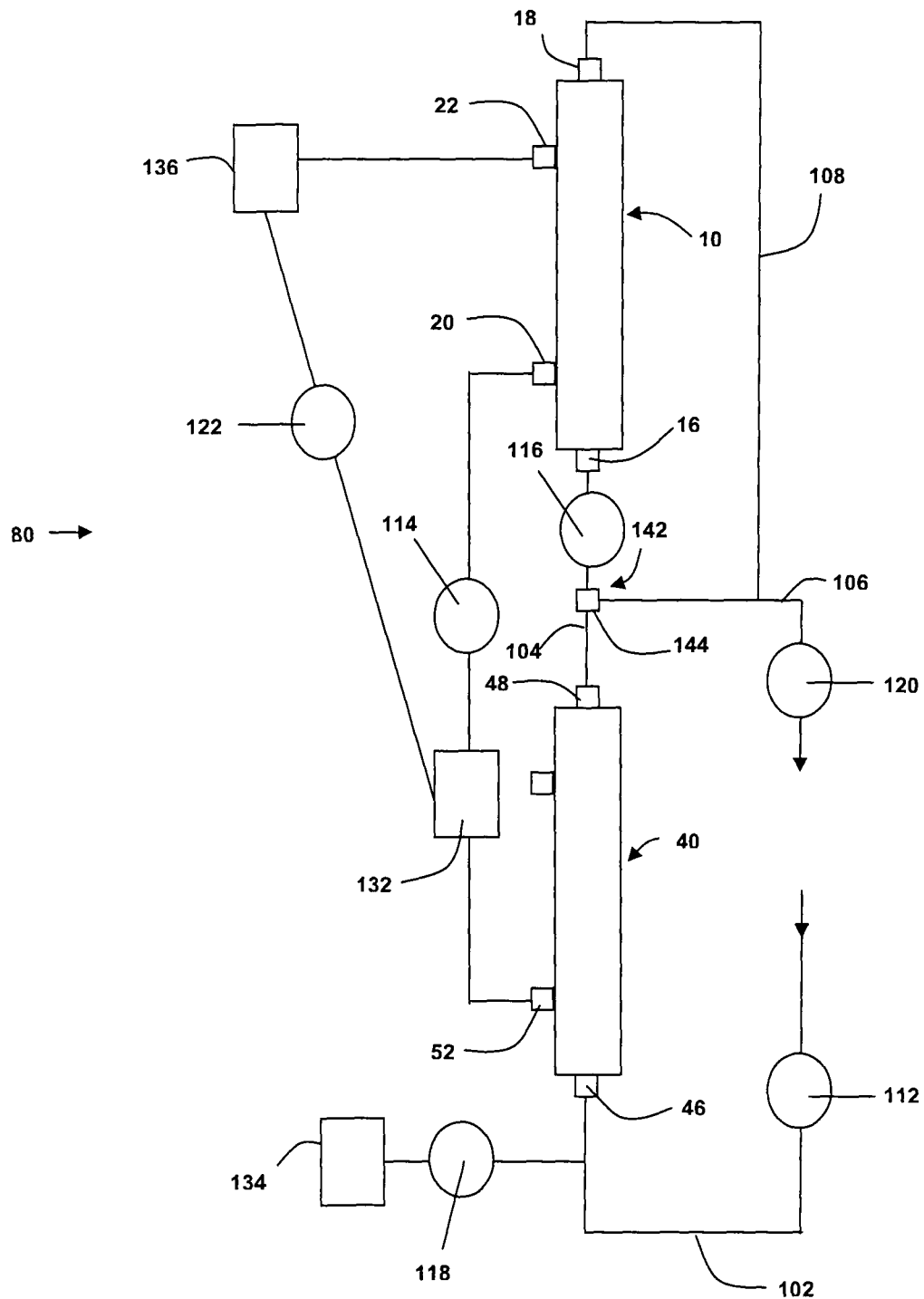

Thus, as depicted in FIG. 4, the bioartificial kidney device 80 may optionally further comprise a first fluid line 102. First fluid line 102 connects with hemofiltration device 40 via blood inlet port 46. Thus, first fluid line 102 may also be connected to the bloodstream of a subject when bioartificial kidney device 80 is in use. Bioartificial kidney device 80 may therefore further comprise a first pump 112 located along first fluid line 102 for controlling the blood flow rate from the subject into bioartificial kidney device 80.

Bioartificial kidney device 80 may optionally further comprise first reservoir 132 for holding hemofiltrate solution. First reservoir 132 may be in fluid communication with hemofiltrate outlet port 52, and also in fluid communication with hemofiltrate inlet port 20 of bioreactor device 10, for example, lying along a fluid line connecting hemofiltrate outlet port 52 with hemofiltrate inlet port 20. Thus, as hemofiltrate exits hemofiltration device 40 it may then flow into first reservoir 132, and eventually from first reservoir 132 and into bioreactor device 10.

Bioartificial kidney device 80 therefore optionally may further comprise second pump 114, for controlling the flow rate of hemofiltrate from the first reservoir 132 to bioreactor device 10. Second pump 114 may therefore be located along a fluid line connecting hemofiltrate outlet port 52 with hemofiltrate inlet port 20, for example downstream of first reservoir 132.

In addition, bioartificial kidney device 80 may optionally further comprise a second fluid line 104 that connects the blood outlet port 48 of the hemofiltration device 40 with the blood inlet port 16 of the bioreactor device 10. A third fluid line 106 may also be included in bioartificial kidney device 80, the third fluid line 106 connected to second fluid line 104 at a branch point 142. The third fluid line 106 also is connected to the bloodstream of the subject, thus allowing at least a portion of the blood exiting hemofiltration device 40 to flow back into the patient without being first flowed through bioreactor 10.

To control the flow of blood once exited from hemofiltration device 40, bioartificial kidney device 80 may optionally further comprise three way connector 144 at the branch point 142, for example, a three way valve. In this way, it is possible to adjust the portion of blood flowing from the blood outlet port 48 of the hemofiltration device 40 to blood inlet port 16 of the bioreactor device 10 and the portion of blood that is diverted away from bioreactor device 10 into the third fluid line 106.

If desired, third pump 116 may also be included for controlling blood flow into blood inlet port 16 of bioreactor device 10. Third pump 116 may be located along second fluid line 104, for example downstream of the branch point 142 but upstream of blood inlet port 16.

In addition, bioartificial kidney device 80 may optionally further comprise a fourth fluid line 108 which is in fluid communication with blood outlet port 18 of bioreactor device 10, and which also connects to third fluid line 106, which is then ultimately connected to the bloodstream of the subject.

Bioartificial kidney device 80 may also include second reservoir 134, for holding replacement fluid. Second reservoir 134 may be in fluid communication with blood inlet port 46, so that replacement fluid mixes with blood and enters into hemofiltration device 40. Alternatively, second reservoir 134 may be located along third fluid line 106, so that replacement fluid can be mixed in with blood prior to being pumped back into the subject's bloodstream. A fourth pump 118 may be included in bioartificial kidney device 80 to control the flow rate from the second reservoir 134. In this way, the amount replacement fluid that is mixed with the blood can be controlled and adjusted as necessary.

In addition, the bioartificial kidney device may further include additional pumps and reservoirs, to assist with clinical operation.

Thus, bioartificial kidney device 80 may include fifth pump 120 for controlling the blood flow rate from the third line 106 back into the subject's bloodstream. Thus, fifth pump 120 may be located along third line 106, upstream of the point where third line 106 connects to the subject.

The bioartificial kidney device 80 may further comprise a third reservoir 136, for collecting waste from the bioreactor device 10. Third reservoir 136 may be in fluid communication with the hemofiltration outlet port 22 of the bioreactor device 10. Thus, waste hemofiltrate solution that has been processed by hemofiltration device 40 and bioreactor device 10 can be collected as it exits bioartificial kidney device 80. The third reservoir 136 may also be in fluid communication with the first reservoir 132, and the bioartificial kidney device 80 may further comprise a sixth pump 122 along a fluid line connecting the third reservoir 136 and first reservoir 132 for controlling flow rate from the third reservoir 136 to the first reservoir 132.

Various hemofiltration cartridges are commercially available and may be used either as the hemofiltration device in the described BAK, or may be modified for use as the bioreactor device. For example, the hemofiltration device may be a high flux hemofiltration cartridge. The bioreactor device may be a high flux pediatric hemofiltration cartridge. The use of high flux cartridges may allow for more efficient exchange of molecules with a relatively high molecular weight. In some embodiments of the described BAK, the bioreactor device may be designed to have a smaller volume than the hemofiltration device.

Figure 5:
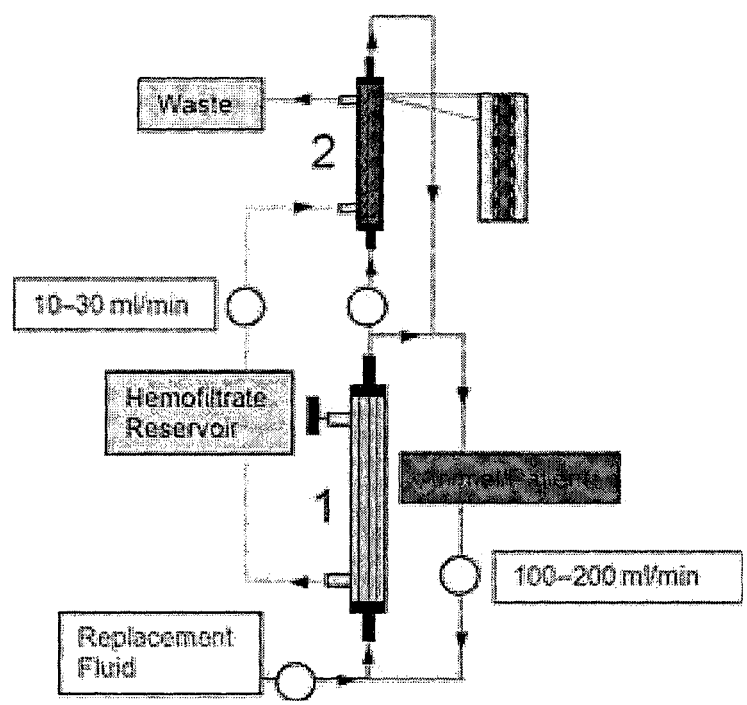
FIG. 5. BAK design.

The described BAK design may be useful for large animal and clinical applications as depicted in FIG. 5. In such embodiments, a standard commercial hemofilter is used as the hemofiltration device. Typically, blood flow rate through such a unit would be in the range of about 100 to about 200 ml/min. Under these conditions about 10 to about 30 ml hemofiltrate/min may be obtained. The hemofiltrate, as well as blood exiting the hemofiltration device, would flow into the bioreactor device. In contrast to previous approaches, the flow rates of the blood and the hemofiltrate entering the bioreactor device could be adjusted to be approximately the same, for example in the range of 10-30 ml/min. By keeping the flow rates approximately equal, transmembrane pressure in the bioreactor device could be reduced or eliminated.

By using a reduced flow rate of blood into the bioreactor device, a major portion of the blood when exiting the hemofiltration device may need to be diverted back to the subject. Thus, a minor portion of blood may flow into the bioreactor device, while a major portion of the blood is not immediately exposed to both cartridges of the bioartificial kidney. This arrangement may improve hemocompatibility, for example by reducing hemolysis and thrombus formation. As well, if necessary, the bioreactor device portion of the BAK may be quickly decoupled, allowing for continued treatment using only the hemofiltration cartridge.

Thus, in another aspect, there is provided a method of using the described bioartificial kidney device to provide renal function to a subject. The method may be performed in a clinical or laboratory context, and may be used by or on outpatients.

The subject may be any subject in which renal function is to be provided, including a subject in need of renal replacement therapy or in need of provision of renal function. For example, the subject may be a subject suffering from a renal disorder, or the subject may be a laboratory animal in which renal treatment is to be tested. The subject may be an animal, including a human.

In the method, the bioartificial kidney device 80 is connected to the subject in order to provide hemofiltration of the subject's blood.

First fluid line 102 is connected to the subject to flow blood from the subject's bloodstream into the bioartificial kidney device 80. Once treated by flowing through the device, the outflowing blood from bioartificial kidney device 80 is flowed back into the subject via the connection of third fluid line 106 to the subject's bloodstream.

In order to control the rate of blood flow, first pump 112 may be used. Blood flow into the hemofiltration device 40 may be adjusted in order to obtain a desirable rate of hemofiltration flow out of hemofiltration device 40. Thus, blood flow from the subject into blood inlet port 46 may be from about 100 ml/min to about 200 ml/min. Depending on the particular hemofiltration device and conditions used, such a flow rate may generate hemofiltrate at a rate of about 10 ml/min to about 30 ml/min.

The rate of flow of hemofiltrate into bioreactor device 10 via hemofiltrate inlet port 20 may be controlled by second pump 114. For example, hemofiltrate may flow from hemofiltrate outlet port 52, optionally into and out from first reservoir 132 and then to hemofiltrate inlet port 20. The rate of flow into hemofiltrate inlet port 20 may be from about 10 ml/min to about 100 ml/min, or about 10 ml/min to about 30 ml/min.

The third pump 116 may be used to control blood flow into the blood inlet port 16 of the bioreactor device 10 at a flow rate of from about 10 ml/min to about 100 ml/min, or at a flow rate of from about 10 ml/min to about 30 ml/min. The rate of blood flow into bioreactor device 10 may be selected to be approximately equal to the rate of flow of hemofiltrate into bioreactor device 10 in order to reduce or eliminate transmembrane pressure.

Given the high sensitivity of cells such as HPTC to mechanical stress, it may be important to avoid transmembrane pressure [16, 17] in the bioreactor device incorporated into the BAK. In previous BAK designs, as the flow rate of the hemofiltrate tends to be much lower than the flow rate of the blood, transmembrane pressure is typically generated in the bioreactor unit when all or substantial parts of the blood exiting the hemofilter flow into the bioreactor [1-9].

In the presently described BAKs, it is possible to use similar flow rates for the blood and the hemofiltrate into the bioreactor portion, which would reduce or prevent the generation of transmembrane pressure. The size of the bioreactor should be adjusted accordingly, and thus may be selected to be smaller than the hemofiltration device. The use of normal paediatric cartridges for the bioreactor device might not be possible because of the requirement to densely pack the HFMs into the small cartridges, and the use of cartridges with a lower density of HFM may be recommended.

When the flow rates of the hemofiltrate and the blood through the bioreactor are similar or approximately equal, a major portion of the blood exiting the hemofiltration device will not be able to enter the bioreactor device. Thus, the major blood portion exiting the hemofiltration device can be flowed back into the subject. This approach would further improve hemocompatibility, as most of the blood would not be exposed to both cartridges.

Should problems arise with low flow rates and small HFM luminal surface areas the bioreactor device, processed hemofiltrate exiting the bioreactor could be recycled and pumped back from the waste reservoir to the hemofiltrate reservoir. This would allow for an increase in the flow rates of the hemofiltrate and the blood through the bioreactor, thus allowing for an increase the size of the bioreactor. Furthermore, such recycling of the hemofiltrate would increase exposure of the hemofiltrate to the cell layer in the bioreactor, which could improve renal function of the BAK. As well, replacement fluid could be added to the hemofiltrate entering the bioreactor, which would also allow for an increase in the flow rates through the bioreactor. Both methods for increasing the flow rates could be combined.

An open question is whether the efficacy of BAK treatment would be compromised by flowing a major portion of the blood from the device directly back into the subject, with only a minor portion of the blood that leaves the hemofiltration device entering the bioreactor. Under these conditions, where less blood would be exposed to the bioreactor as compared to previous BAK designs. The precise mechanism for improved survival of critically ill patients with AKI [9] and also improved survival in respective animal models [2, 5-7] in response to BAK treatment are unclear. Reabsorption functions of the proximal tubular cells, for which larger cell numbers would be required [25], would not be expected to play a major role in this situation [1]. It has been speculated that immunomodulatory functions of the BAK are important. Some results suggested that in particular the levels of IL-6 and IL-10 play a role [1, 2, 5-8]. As previous studies measured the serum or plasma levels of cytokines during BAK treatment it remained unclear whether and how cytokine levels were influenced by the cells in the bioreactor.

As set out in the examples below, IL-6 and IL-8 may be released from the bioreactor in the presently described BAK. In particular, high levels of IL-6 may be produced, for example at concentrations approximately 100- to 1000-fold higher than normal circulating IL-6 levels in humans. Without being limited by theory, it could be expected that BAK treatment may have immunomodulatory effects, as observed in previous studies [1, 2, 5-8].

Although when HPTCs are used as the cells in the bioreactor, the bioreactor does not appear to release IL-10. However, it has been observed after injection of recombinant human IL-6 into healthy volunteers that the levels of two anti-inflammatory cytokines, including IL-10, were increased by IL-6 [31]. Such effects of IL-6 may explain the increased levels of IL-10 that have been observed in animals during BAK treatment [1, 2]. Typically, IL-6 acts at distant sites and the effects of BAK treatment on cytokine expression patterns in peripheral blood mononuclear cells might be also explained by such effects [7]. It is not clear why HPTC produced high IL-6 levels under normal conditions, but this phenomenon has been observed fairly consistently. This production of IL-6 may reflect a reaction by the cells to the in vitro conditions, which are quite different from the normal in vivo environment in the kidney.

No significant increase in the levels of IL-6 and IL-8 was observed after prolonged exposure to LPS for 24 hrs, which is in agreement with a previous study that found no significant effects of LPS on the levels of IL-6 produced by HPTC (called PTEC in this reference) [32]. HPTCs have been shown to significantly increase secretion of IL-6 and IL-8 in response to other stimuli, such as exposure to IL-1a [32] or different kinds of insults. However, HPTCs appear to be only minimally responsive to LPS, which has been applied in BAK-related animal studies [1, 7]. Nevertheless, although no direct effect of LPS on HPTCs has been found, indirect effects on cytokine production by HPTCs during animal experiments cannot be excluded.

The present methods and uses are further exemplified by way of the following non-limiting examples.

EXAMPLES

Example 1

A novel bioartificial kidney was designed in an attempt to improve upon various properties of existing devices, including hemocompatibility and cell performance. An notable feature of the novel design is confinement of the blood to the lumina of the hollow fibre membranes; such a feature avoids exposure of the blood to the non-hemocompatible outer surfaces of hollow fibre membranes, in contrast to the design of previous bioartificial kidneys. In the novel BAK design, the rough outer surfaces of the hollow fibres were used as substrate for cell growth.

The results show that commercial hollow fibre membranes can be directly applied in the bioreactor when human primary renal proximal tubular cells are grown in the above-described configuration, and no coatings are required for the formation of robust and functional renal epithelia.

Furthermore, the results demonstrate that the bioreactor unit produces significant amounts of interleukins. This result helps to understand the immunomodulatory effects of bio-artificial kidneys, which have been observed previously.

Materials and Methods

Cell Culture:

Human primary renal proximal tubular cells, the porcine proximal tubular-derived cell line LLC-PK1 and the murine fibroblast cell line NIH 3T3 were obtained from the American Type Culture Collection (ATCC, Rockville, Md., USA) and cultivated as described [12, 18]. HPTC were used up to passage 5.

Static Culture and Double Coating of HFM:

Highflux polyarylethersulfone (PAES) HFM were obtained from the hemofilter of the PrismafleX™ HF20 set (Gambro Singapore, Singapore) and highflux polysulfone (PSF) HFM were derived from the HF80S hemofilter (Fresenius Medical Care, Bad Homburg, Germany). HFM consisting of polyethersulfone/polyvinylpyrrolidone (PES/PVP) were produced as described [12]. HFM and glass capillaries (Sutter Instrument, Novato, Calif., USA) were sterilized with 70% ethanol and UV irradiation in 24-well tissue culture plates (Nunc, Naperville, Ill., USA), and were subsequently washed with phosphate-buffered saline (PBS). After cell seeding the samples were gently agitated for 4 hrs on a shaker that was placed in an incubator. Cell culture medium was changed on the following day and the cells were cultivated for 3 days. In some experiments the outer surfaces of the HFM were double coated with DOPA and collagen IV as described [12, 13].

Scanning Electron Microscopy (SEM), Immunostaining and Determination of c-Glutamyl Transferase (GGT) Activity:

These methods were performed as described [12].

Quantitative Real-Time Polymerase Chain Reaction (qPCR):

Quantitative real-time polymerase chain reaction (qPCR) was performed as described [12, 19].

HFM Bioreactors:

Highflux PAES HFM with an inner diameter of 215 ipm and a wall thickness of 50 μm (Gambro Singapore) were applied in all bioreactors. Small bioreactors containing 1 single HFM and medium-sized bioreactors with 25 HFM were constructed with polypropylene housings made from 1 ml syringes (B. Braun Melsungen AG, Melsungen, Germany). Larger bioreactors containing 250 HFM were constructed with a polypropylene housing made from 10 ml syringes. HFM were glued to gas-permeable tubings (PharMed BPT tubing, Cole-Parmer, Vernon Hills, Ill., USA) in the small and medium-sized bioreactors for luminal perfusion. For construction of the larger bioreactors luerlock tips of 5 ml syringes were glued to the HFM for luminal perfusion. HFM connected to tubings or luer-lock tips were glued together with gas permeable tubings for extra-HFM perfusion into the polypropylene housings. Three-way male lock stopcocks were inserted into the inlet and outlet tubings of intra- and extra-HFM circuits for sample collection and cell seeding. Perfusion was driven by a multi-channel peristaltic pump (Ismatec, Glattbrugg, Switzerland).

HFM Bioreactor Handling and Cell Seeding:

Before cell seeding HFM bioreactors were perfused (1 ml/min.) with 70% ethanol for 8 hrs and subsequently with sterile PBS overnight. The cell suspension with $3 \times 10^6$-$5 \times 10^6$ cells/ml was injected into the extra-HFM space. The following volumes of cell suspension were used for cell seeding: 600 μl (25-HFM bioreactor), 4.0-4.5 ml (250-HFM bioreactor) and 30-35 ml (commercial hemofilter). After cell seeding the bioreactor was rotated by 90 degrees every 2 hrs and rotation was performed three times. Perfusion started 2 hrs after the last rotation and was performed with cell culture medium at a flow rate of 80 μl/min. unless indicated otherwise. Perfusion was continued for 7 days before the assays were performed.

Lucifer Yellow Uptake and Transport:

The extra-HFM space of HPTC-containing 25-HFM bioreactors was perfused with normal cell culture medium, whereas HFM lumina were perfused with cell culture medium containing 80 μM of lucifer yellow. Perfusion was performed for 24 hrs at flow rates of 80 μl/min. The same conditions were applied to 25-HFM cartridges without cells that were used as controls. After 24 hrs of perfusion samples from the extra-HFM space were collected. The fluorescence intensity was measured by using a microplate reader (Tecan Safire2™, Mannedorf, Switzerland) with excitation and emission wavelengths of 428 and 540 nm respectively. To assess cellular uptake of lucifer yellow HFM derived from the bioreactors were fixed with formaldehyde (3.7% in PBS) and stained with 4',6-diamidino-2-phenylindole (DAPI) for epifluorescence microscopy. From some of the HFM, the cells were detached with trypsin-versene, fixed with formaldehyde and stained with DAPI. Epifluorescence imaging was performed by using an Olympus BX-DSU microscope (Olympus, Tokyo, Japan).

Determination of the Back-Leak of Urea and Creatinine:

Extra-HFM spaces of 25-HFM bioreactors were perfused with cell culture medium containing 2 mg/ml of urea (Invitrogen, Singapore) and 0.1 mg/ml of creatinine (Sigma-Aldrich, Singapore). The luminal spaces were perfused with normal cell culture medium without urea and creatinine. Perfusion was performed for 4 hrs at flow rates of 80 μl/min. Samples from both compartments were collected and the concentrations of urea and creatinine were measured with an i-STAT analyser (Abbott Point of Care Inc., Princeton, N.J., USA).

Cytokine Release:

The extra-HFM space of 25-HFM bioreactors was perfused with cell culture medium containing 10 μg/ml of lipopolysaccharides (LPS) from *Escherichia coli* (Sigma-Aldrich). Control bioreactors were perfused with normal cell culture medium. The bioreactors were perfused for 24 hrs at flow rates of 80 ll/min. Interleukin-6 (IL-6), IL-8 and IL-10 levels in the cell culture medium were determined after 24 hrs by using human IL-6, IL-8 and IL-10 ELISA kits (Life Technologies, Singapore).

Exposure to Hemofiltrate with a Relevant Perfusion Rate:

Hemofiltrate was prepared from inactivated human serum (Invitrogen) by using Vivaspin 20 hemofiltration devices (Sartorius AG, Goettingen, Germany) with a molecular weight cut-off of 30 kD. The extra-HFM space of 25-HFM bioreactors was perfused with the hemofiltrate at a flow rate of 0.5 ml/min. for 16 hrs. At this flow rate, velocity and shear stress on the cells in a 25-HFM bioreactor are the same as in a PrismafleX HF20 hemofilter when a flow rate of 10 ml/min. is applied. After 16 hrs cell performance was assessed by epifluorescence microscopy, immunostaining and determination γ-glutamyl transferase (GGT) activity.

Statistics:

All statistical analyses were performed using the SigmaStat™ (3.5) software (Systat Software Inc., Chicago, Ill., USA). All the data were tested for normal distribution and the test was passed in all cases. The student's two-tailed t-test was used for determining significance levels and at least three replicates were included in each experiment. Significant differences (P<0.05) are marked with an asterisk in the graphs.

Results

BAK Design:

The BAK design for large animal and clinical studies used in these experiments is illustrated in FIG. 5. The first unit is a normal commercial hemofilter, and the blood flow rate used was in the range of 100-200 ml/min. Under these conditions approximately 10-30 ml hemofiltrate/min were obtained. The hemofiltrate, as well as blood exiting the hemofilter, was flowed into the bioreactor. The flow rates of the blood and of the hemofiltrate entering the bioreactor were approximately the same and in the range of 10-30 ml/min in order to eliminate or reduce transmembrane pressure in the bioreactor.

HPTC performance when grown on the outer surfaces of commercial HFM was investigated and it was assessed whether under these conditions membrane coatings were still required.

Figure 6:
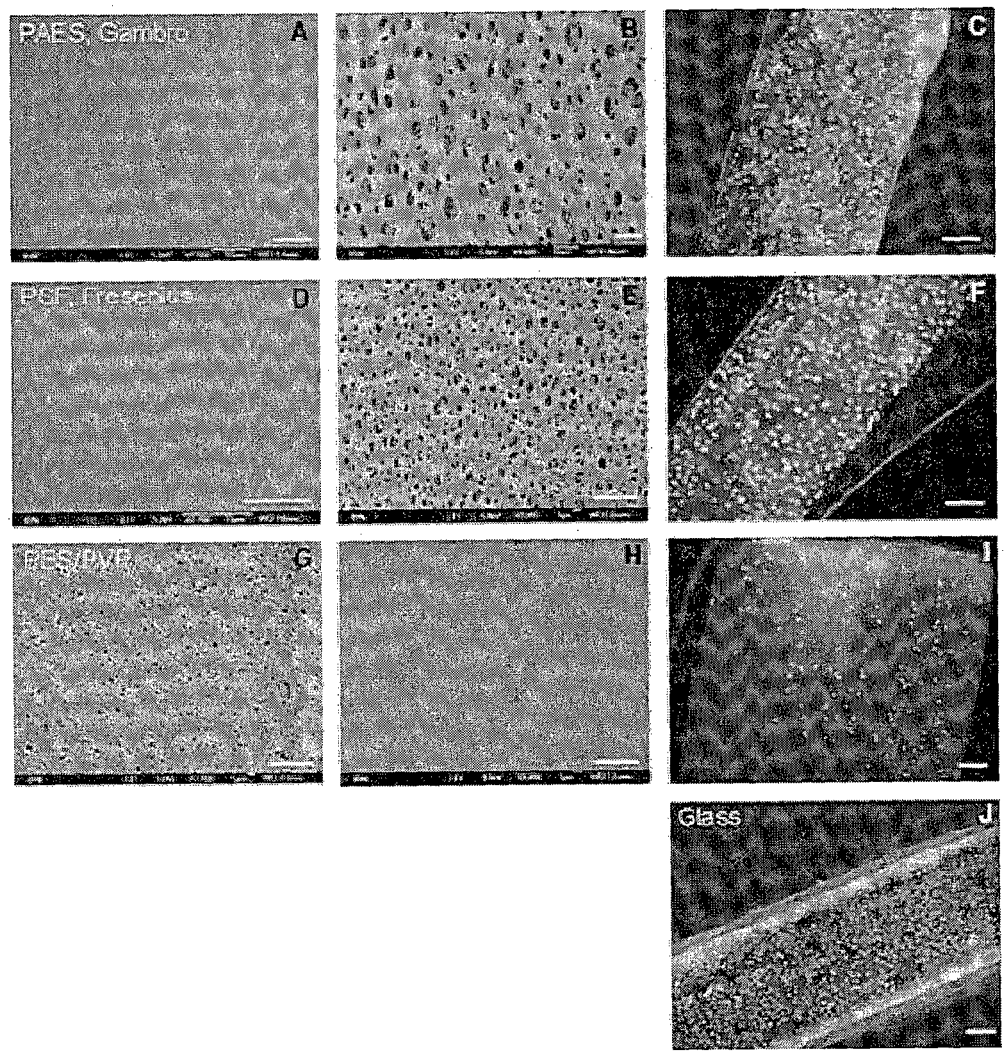
FIG. 6. Cell growth on HFM. Each row shows SEM images of the inner (left-hand panels; A, D and G) and the outer (middle; B, E and H) surface of HFM and an epifluorescence image of the DAPI-stained nuclei (white spots) of HPTC grown on the outer surface of the respective HFM (C, F and I). A glass capillary (positive control) with HPTC grown on the outer surface (DAPI-stained nuclei: white spots) is shown in (J). The different rows show HFM consisting of PAES (Gambro; A, B and C), PSF (Fresenius; D, E and F) and PES/PVP (non-commercial, G, H and I). HFM consisting of PES/PVP (outer diameter: 780 lm) were used as negative control and only few cells survived on this material (I), whereas confluent monolayers were formed on the outer surfaces of all other materials (C, F and J). The inner surfaces of the commercial HFM consist of the smooth skin layer (A and D), whereas their outer surfaces are rough with relatively large pores (B and E). The PES/PVP HFM have a rough and microporous inner surface (G) and the smooth skin layer is on the outer surface (H) [12]. Scale bars: A, B and D: 10 μm; E, G and H: 5 μm; C and F: 100 μm; I and J: 200 μm (HFM were squeezed and flattened for epifluorescence microscopy).

HPTC Performance on the Outer Surfaces of Unmodified Commercial HFM:

To HPTC performance on the outer surfaces of HFM, HFM consisting of PSF or PAES were used. These HFM, which were derived from commercial hemofilters, showed the typical architecture and the inner surface consisted of the smooth skin layer, whereas the outer surface was rough with relatively large pores (FIGS. 6A, B, D and E). Unmodified commercial HFM that were not coated before cell seeding were used in the following experiments.

In a first set of experiments, HPTC were grown on the outer surfaces of the HFM in static culture. After 3 days, a confluent epithelium was formed (FIGS. 6C and F). A similar epithelium was obtained with glass capillaries, which served as positive control (FIG. 6J), since unmodified glass is an excellent substrate for HPTC [14, 20]. In contrast, only few cells were observed on HFM consisting of PES/PVP (FIG. 6I), which were used as negative control. The PES/PVP HFM used here have a reversed architecture and the smooth skin layer is on the outer surface (FIG. 6H) [12]. HPTC performance is compromised on this material in the absence of coating [12].

Figure 7:
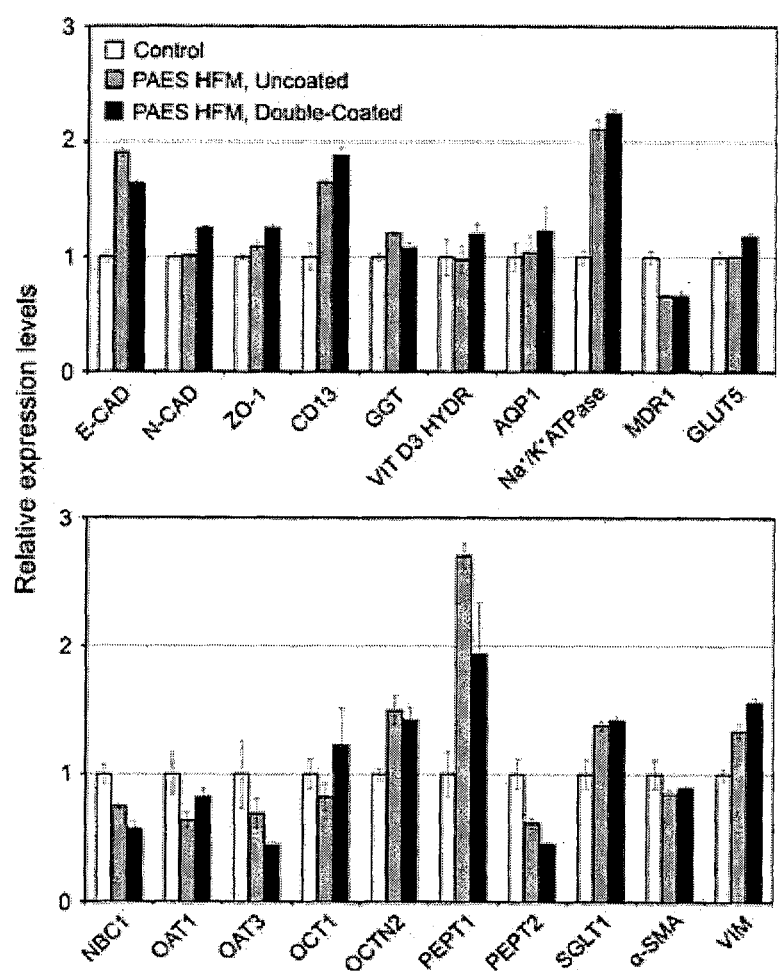
FIG. 7. Marker gene expression determined by qPCR. The relative expression levels of the genes indicated (x-axis) were assessed with HPTC that were cultivated for 3 days on uncoated (grey bars) or double-coated with 3,4-dihydroxy-L-phenylalanine (DOPA) and collagen IV (black bars) commercial HFM consisting of PAES. The bars show the mean+/−SD (n=3) and the mean values obtained with HPTC cultivated on TCPS (control) were set to 1 (white bars). The genes coding for the following epithelial and HPTC-specific markers were included here: E-cadherin (E-CAD), N-cadherin (N-CAD), zonula occludens 1 (ZO-1), aminopeptidase N (CD13), g-glutamyl transferase (GGT), 25-hydroxyvitamin D3 1α-hydroxylase (VIT D3 HYDR), aquaporin-1 (AQP1), Na+/K+ ATPase, multidrug resistance gene 1 (MDR1), glucose transporter 5 (GLUT5), Na+HCO3-co-transporter 1 (NBC1), organic anion transporter 1 (OAT1), OAT3, organic cation transporter 1 (OCT1), organic cation/carnitine transporter 2 (OCTN2), proton-coupled peptide transporter 1 (PEPT1), PEPT2 and sodium-dependent glucose co-transporter 1 (SGLT1). Expression levels of the myofibroblast marker α-smooth muscle actin (α-SMA) and the mesenchymal cell marker vimentin (VIM) were also determined.

Human primary renal proximal tubular cells performance on synthetic membranes is usually improved by coatings, but cell growth and survival were not obviously negatively affected on the outer surfaces of uncoated commercial HFM. To address subtle potential effects on cell performance, gene expression patterns were examined (FIG. 7). The expression levels of 20 marker genes were determined by qPCR. This assay is well established and has been applied before to characterize HPTC performance [12, 14, 19]. Genes coding for the following epithelial and HPTC-specific markers were included here: E-cadherin (E-CAD), N-cadherin (NCAD), zonula occludens 1 (ZO-1), aminopeptidase N (CD13), GGT, 25-hydroxy vitamin D3 1a-hydroxylase (VIT D3 HYDR), aquaporin-1 (AQP1), Na+/K+ ATPase, multidrug resistance gene 1 (MDR1), glucose transporter 5 (GLUT5), Na+HCO3_co-transporter 1 (NBC1), organic anion transporter 1 (OAT1), OAT3, organic cation transporter 1 (OCT1), organic cation/carnitine transporter 2 (OCTN2), proton-coupled peptide transporter 1 (PEPT1), PEPT2 and sodium dependent glucose co-transporter 1 (SGLT1). We also determined expression levels of the myofibroblast marker a-smooth muscle actin (a-SMA) and the mesenchymal cell marker vimentin (VIM).

Human primary renal proximal tubular cells were grown on commercial PAES HFM, which remained uncoated or were double coated with DOPA and collagen IV. A double coating consisting of DOPA/collagen IV supports HPTC performance on synthetic membranes better than coatings consisting of a single extracellular matrix protein [13]. Control cells were grown on tissue culture plastic (TCPS), which is an excellent substrate for HPTC [14]. Some differences in gene expression patterns were observed when cells were grown either on uncoated PAES HFM or on TCPS, which indicated some impact of the different substrates on cell performance. However, in most cases, the expression levels of epithelial and HPTC-specific markers on PAES HFM were at least as high as in the positive control (FIG. 7). This result was in agreement with the previous findings (see above) that overall HPTC performance was not compromised when cells resided on uncoated PAES HFM. Double coating did not improve marker gene expression. Together, these results suggested that the uncoated outer surfaces of commercial HFM were suitable substrates for HPTC and that HPTC performance could not be further improved by applying a coating to these surfaces.

Figure 8:
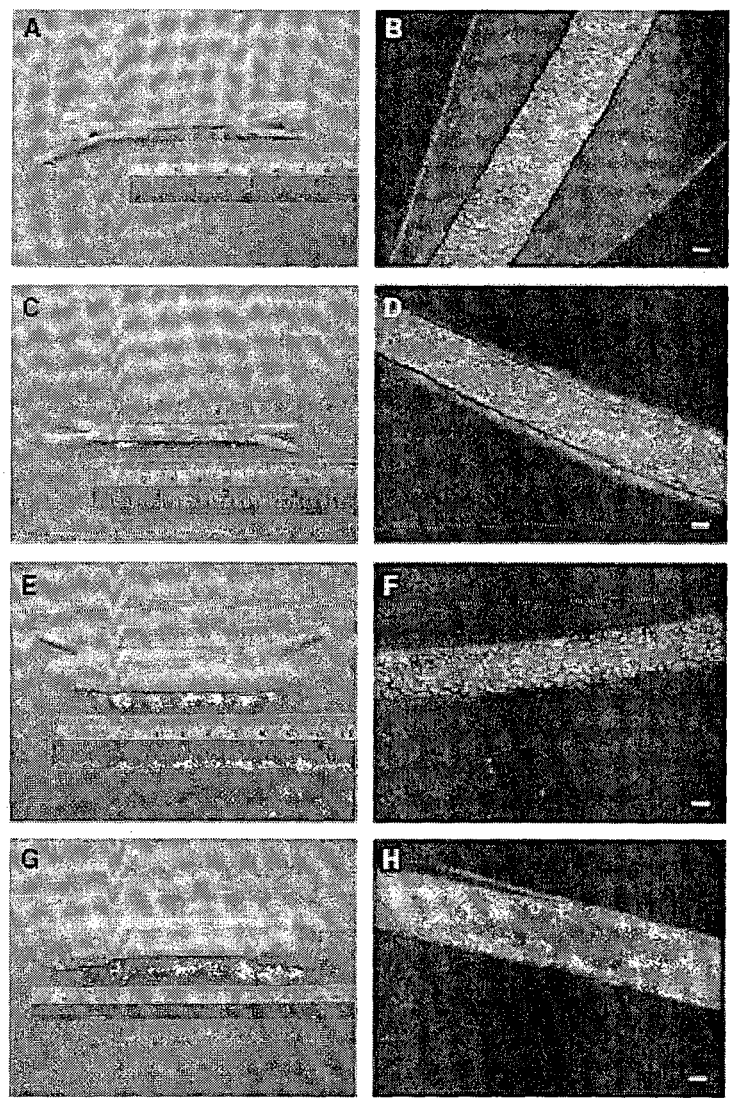
FIG. 8. HPTC growth in bioreactors. The bioreactors are shown on the left-hand panels (A, C, E and G). All bioreactors contained uncoated commercial PAES HFM derived from the hemofilter of the PrismafleX HF20 set (Gambro). The bioreactors contained one single HFM (A), 25 HFM (C) or approximately 250-300 HFM (E). In addition, the unmodified hemofilter from the PrismafleX HF20 set (Gambro) comprising approximately 2600 HFM was used (G). The right-hand panels (B, D, F and H) show single HFM derived from the bioreactors shown on the left after HPTC had been seeded on the outer HFM surfaces and cultivated for 7 days. Cell nuclei were stained with DAPI and appear as white spots on the grey scale images. HPTC formed confluent monolayers when home-made bioreactors were used (B, D and F). In contrast, only few cells survived in the commercial cartridge with densely packed HFM (H). Ruler in A, C, E and F: cm (white scale) and inch (grey scale); scale bars in B, D, F and H: 100 μm (HFM were squeezed and flattened for epifluorescence microscopy).

HPTC Performance in Bioreactors:

Next, uncoated and unmodified PAES HFM were mounted into cartridges and HPTC performance on the outer surface was tested under bioreactor conditions. As the work was based on primary cells, small cartridges containing 1 single HFM (FIG. 8A) were used as a starting point. HPTC were seeded on the outer HFM surfaces and perfusion of the extra-HFM space started 8 hrs after seeding with a flow rate of 80 µl/min. A confluent epithelium was obtained on the HFM after 7 days (FIG. 8B). Experiments were then upscaled to a larger bioreactor containing 25 HFM (FIG. 8C). Again, a confluent epithelium was obtained after 7 days (FIG. 8D). Cells were then seeded into the commercial cartridge (hemofilter from PrismafleX HF20 set, Gambro) containing approximately 2600 HFM (FIG. 8G) with a packing density of approximately 683 HFM/cm$^2$. Here, the outer surfaces of the HFM were largely devoid of cells after 7 days (FIG. 8H). As the previous experiments had indicated that there were no problems with the HPTC-compatibility of the material, it was assessed whether the dense packing of HFM in the commercial cartridge was the reason for compromised HPTC performance. Therefore, the next series of experiments was performed with a cartridge that contained approximately 250-300 commercial HFM with reduced packing density (approximately 160 HFM/cm$^2$) (FIG. 8E). Under these conditions again a confluent epithelium was obtained after 7 days (FIG. 8F), confirming that indeed dense HFM packing in the commercial cartridge compromised HPTC performance.

Figure 13:
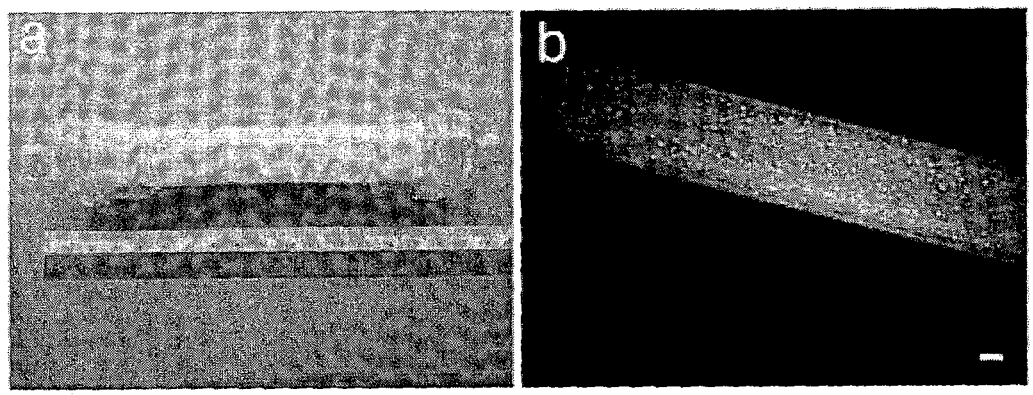
FIG. 13. LLC-PK1 cells were cultivated with perfusion in the unmodified hemofilter from the PrismafleX HF20 set (Gambro) shown in (a). (b) shows the LLC-PK1 epithelium on the outer surface of an HFM removed from the hemofilter after 7 days. DAPI-stained cell nuclei appear as white spots. Ruler in a: cm (white scale) and inch (grey scale); scale bar in b: 100 μm (the HFM was squeezed and flattened for epifluorescence microscopy).

Interestingly, the porcine proximal tubular cell line LLC-PK1 (Lewis lung cancer-porcine kidney 1) was less sensitive to the packing density of the HFM and these cells formed confluent epithelia on the outsides of the uncoated HFM also in the commercial cartridge (FIG. 13).

Figure 14:
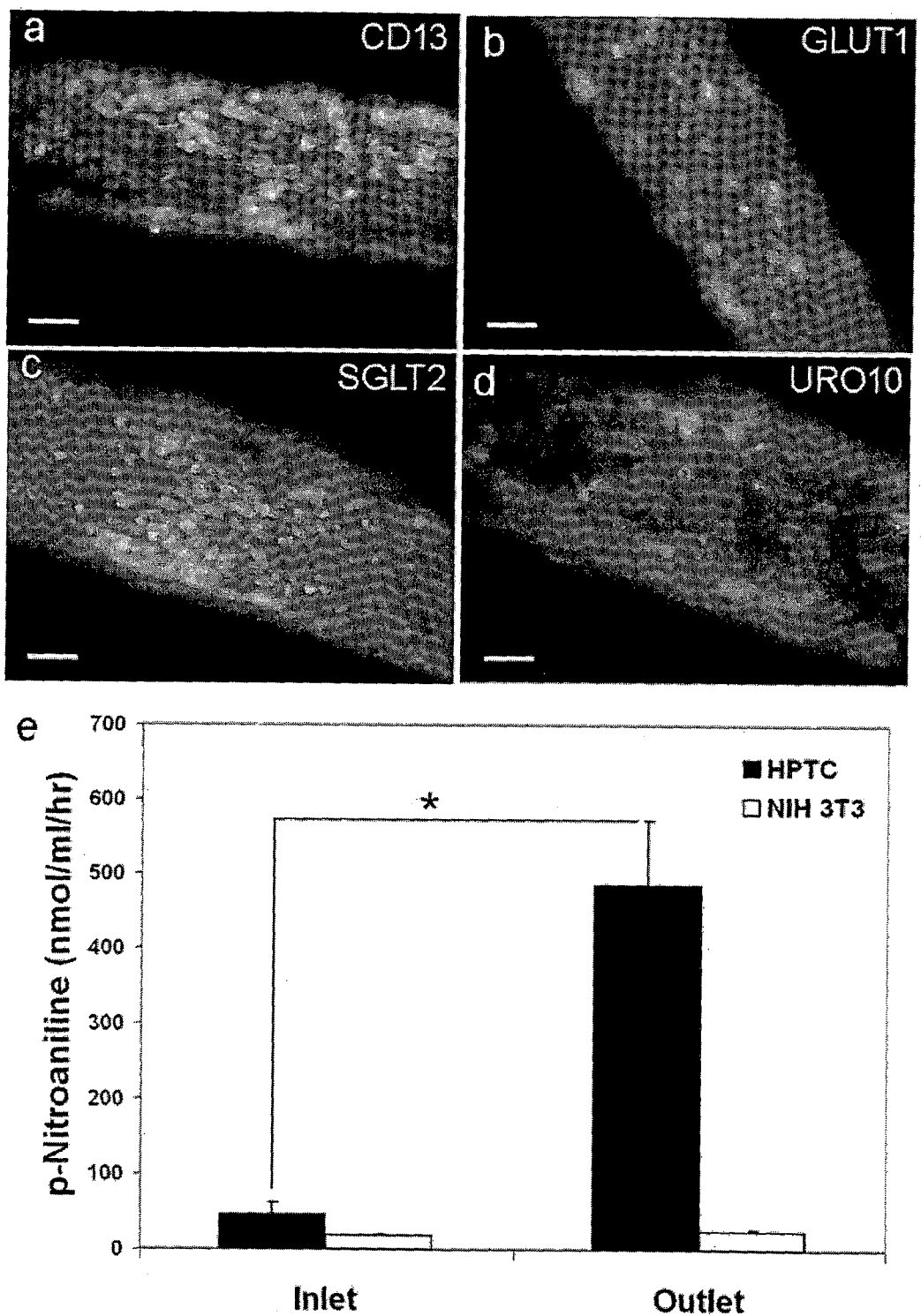
FIG. 14. Expression of marker proteins and brush border enzymes. HPTC were cultivated in 25-HFM bioreactors. Panels (a-d) show confluent epithelia of HPTC on the outer surfaces of PAES HFM. CD13, GLUT1, SGLT2 and URO10 were detected by immunofluorescence (green; cell nuclei: blue). Scale bars: 100 μm. The bars in (e) show the amounts of p-nitroaniline (mean+/−s.d.; n=3), which is generated in a reaction catalyzed by the brush border enzyme GGT. The amounts of p-nitroaniline were measured at the inlet and outlet ports of the bioreactors. Significantly higher amounts (indicated by an asterisk) were measured at the outlet ports in comparison to the inlet ports when the bioreactors contained HPTC (black bars). Similar bioreactors containing NIH 3T3 fibroblasts were used as control (white bars) and here the amounts of p-nitroaniline were always very low.

Organic Anion Transport and Back-Leak of Urea and Creatinine:

The following experiments were performed with medium-sized cartridges containing 25 HFM. The extra-HFM space was perfused with a flow rate of 80 µl/min. Where indicated, the luminal space was perfused at the same rate. It was confirmed by immunostaining that the epithelia formed on the outsides of HFM were well differentiated and expressed characteristic marker proteins and brush border enzymes (FIG. 14). The results showed that most of the cells expressed the brush border enzyme CD13 (aminopeptidase N), the baso-lateral glucose transporter 1 (GLUT1), the sodium dependent glucose co-transporter 2 (SGLT2) and the urothelial glycoprotein 10 (URO10). In addition, HPTC in the bioreactor cartridge showed high activity of the brush border enzyme GGT (FIG. 14).

Figure 9:
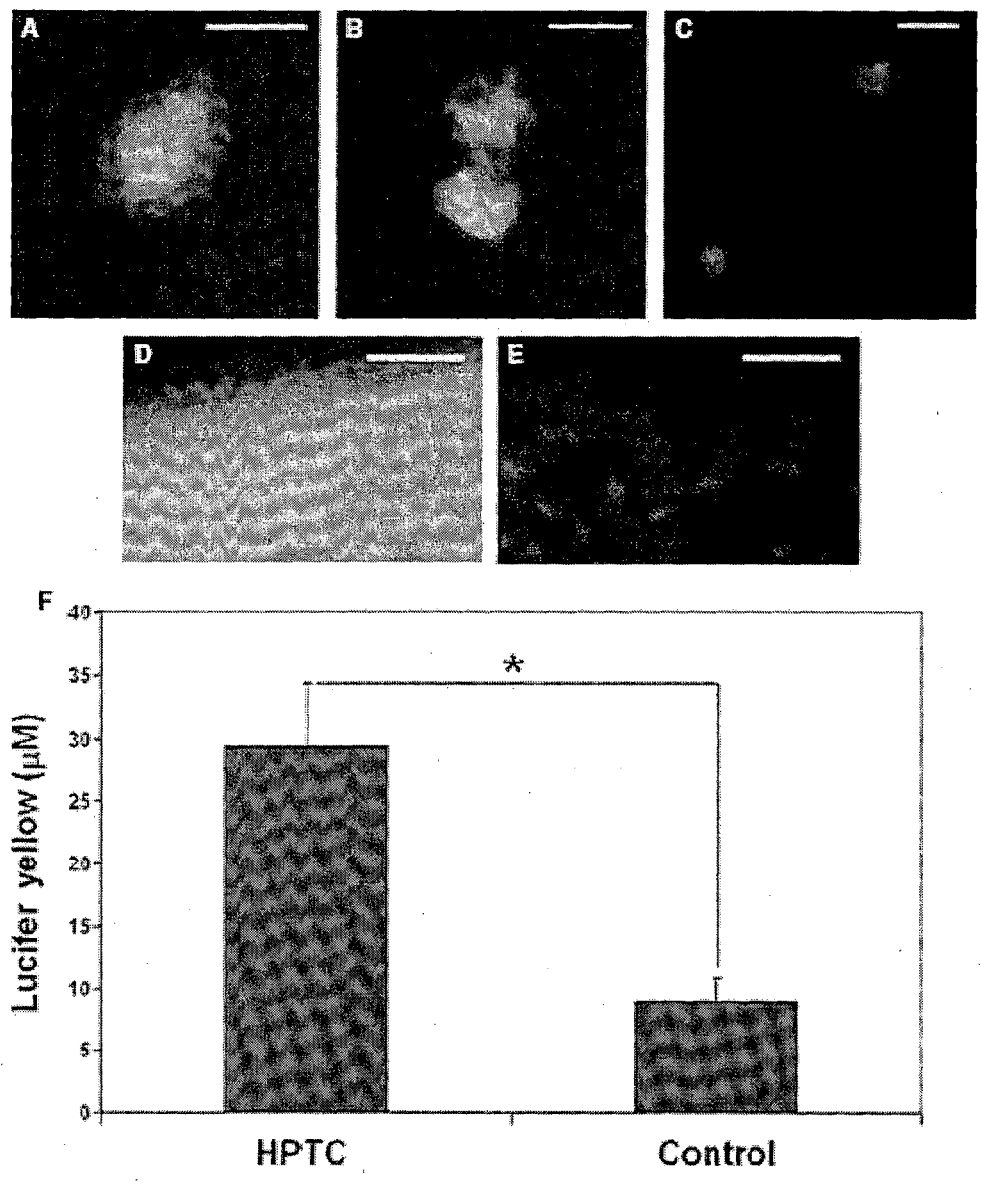
FIG. 9. Baso-lateral cellular uptake and transport of lucifer yellow. HPTC were grown on the outer surfaces of PAES HFM in 25-HFM bioreactors. HFM lumina where perfused with 80 IM of lucifer yellow. The extra-HFM space was perfused with cell culture medium not containing lucifer yellow. (A, B and C) show HPTC that were detached from HFM derived from bioreactors that were perfused (A and B) or not perfused (C) with lucifer yellow (green; cell nuclei: blue). Panels (D) and (E) show HPTC epithelia on the outer surfaces of HFM. The HFM were derived from bioreactors that were perfused (D) or not perfused (E) with lucifer yellow. Scale bars: A, B and C: 25 lm; D and E: 50 lm. The bars in (F) display the concentrations of lucifer yellow (mean_SD; n=3) in the extra-HFM space, after the luminal spaces had been perfused with lucifer yellow for 24 hrs. The bioreactors contained HPTC or did not contain any cells (control). Significant differences are marked with an asterisk.

To test baso-lateral uptake and transport of organic anions, the luminal spaces of the HFM were perfused for 24 hrs with medium containing 80 µM of lucifer yellow at day 8 after cell seeding. The extra-HFM space was perfused with cell culture medium not containing lucifer yellow. Green fluorescence was observed in the cytoplasm of HPTC residing on the outer surface of the HFM confirmed baso-lateral uptake (FIG. 9D). To exclude the assumption that the green fluorescence observed was because of adsorption of lucifer yellow to the membrane, the cells were detached from some HFM after perfusion with lucifer yellow. Single detached cells showed green fluorescence in the cytoplasm, in contrast to control cells from bioreactors that were not perfused lucifer yellow (FIG. 9A-C).

Transport of lucifer yellow was addressed by measuring the concentration of lucifer yellow in the extra-HFM space. When the outer surfaces of the HFM were covered by epithelia formed by HPTC, a significantly higher concentration of lucifer yellow was measured in the extra-HFM space in comparison to control bioreactors devoid of cells (FIG. 9F). The concentration of lucifer yellow in the extra-HFM space was 3.3-fold higher (difference between the mean values) in cell-containing bioreactors in comparison to the controls. Together, the results demonstrated baso-lateral uptake and transport of lucifer yellow by the epithelium covering the HFM.

Figure 10:
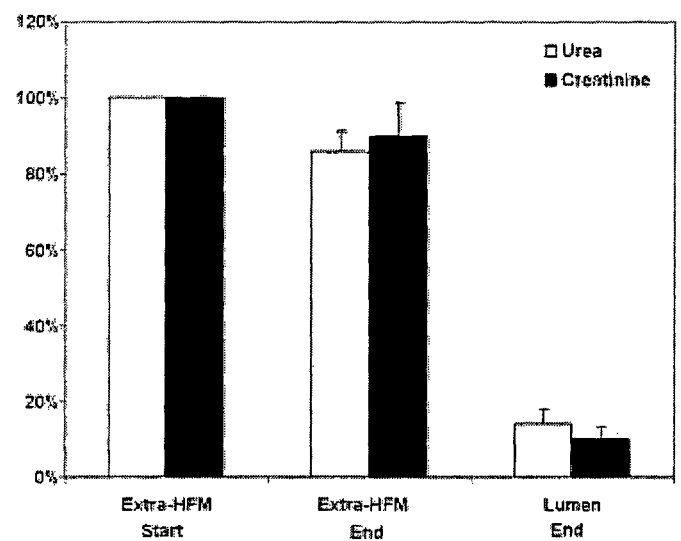
FIG. 10. Back-leak of urea and creatinine. The extra-HFM space of 25-HFM bioreactors was perfused for 4 hrs with cell culture medium containing urea and creatinine, whereas the lumina were perfused with medium not containing these compounds. The bars (mean_SD; n=3) show the relative percentages of urea and creatinine (initial concentrations in the extra-HFM space 100%) in the extra-HFM space at the start of the experiments and at the end after 4 hrs of perfusion. The right-hand bars show the relative percentages of urea and creatinine in the luminal spaces after the 4-hr perfusion period.

After demonstrating transport from the luminal (blood compartment) to the extra-HFM (waste) compartment, it was important to address whether there would be back-leak of waste compounds to the luminal compartment. In a BAK, the waste compartment would contain the hemofiltrate with high concentrations of urea and creatinine. To address the leakiness of the epithelium for these compounds, the extra-HFM space was perfused at day 8 after cell seeding for 4 hrs with medium containing 2 mg/ml of urea and 0.1 mg/ml of creatinine. About 9% (creatinine) and 15% (urea) of these compounds had leaked into the luminal compartment during a time period of 4 hrs (FIG. 10). Previous studies measured during eightfold shorter time periods of 30 min. leakage rates of approximately 15% (urea and creatinine, day 7-17 after cell seeding) [21] and <10% (inulin, at least 14 days after seeding) [22].

Release of Interleukins:

It is believed that the positive effects of BAK treatment may be, at least in part, because of immunomodulatory functions of the device. Here, release of IL-6, IL-8 and IL-10 from the bioreactor was examined after perfusion with 10 µg/ml of LPS for 24 hrs or after perfusion with normal medium not containing LPS. LPS administration was performed in two previously reported in vivo studies where changes in cytokine levels were observed [1, 7] and one study [2] used *E. coli* administration. The conditions under which the other in vivo studies [5, 6] and the clinical trial [8] were performed could not be mimicked in vitro.

Figure 11:
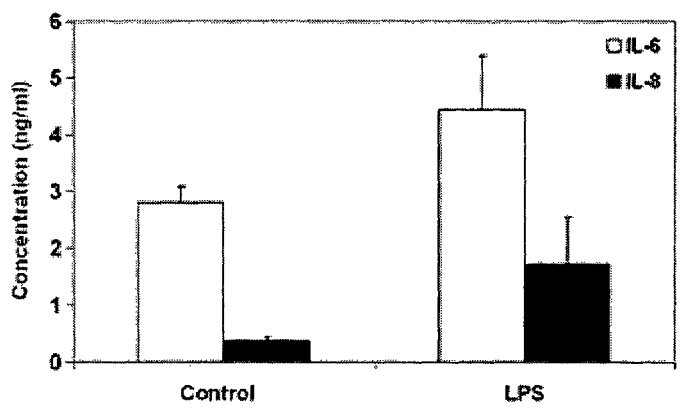
FIG. 11. Cytokine production. 25-HFM bioreactors were perfused with cell culture medium containing 10 lg/ml LPS (right-hand bars), or were perfused with normal cell culture medium not containing LPS (control). The levels of IL-6, IL-8 and IL-10 were measured by ELISA and the bars (mean_SD; n=3) display the concentrations of these interleukins (the levels of IL-10 were always below the detection limit). The levels of IL-6 (white bars) and IL-8 (black bars) were not changed significantly after 24 hrs of LPS stimulation.

Measurements performed by ELISA revealed that the bioreactor released already under normal conditions in the absence of LPS significant amounts of IL-6 and IL-8 (FIG. 11). In particular, high amounts of IL-6 were produced that were in the range of 3 ng/ml. Normal circulating IL-6 levels in humans are approximately 2-3 orders of magnitude lower and are in the range of approximately 1-30 pg/ml [23]. The levels of IL-6 and IL-8 were elevated after LPS treatment and the differences between the mean values of the results obtained in the absence or presence of LPS were 1.6-fold (IL-6) and 4.6-fold (IL-8) respectively. However, these changes were not found to be significant and the standard deviations in the presence of LPS were relatively large (FIG. 11). Under all conditions, the amounts of IL-10 were below the detection limit.

Exposure to Hemofiltrate and Relevant Perfusion Rates do not Compromise HPTC:

In a last series of experiments, conditions were used to mimic conditions in the bioreactor during animal experiments and clinical trials. At day 8 after cell seeding, the 25-HFM bioreactor was perfused with human hemofiltrate instead cell culture medium. The hemofiltrate had been prepared from inactivated human serum. Perfusion with hemofiltrate was performed for 16 hrs. The flow rate of the hemofiltrate in the 25-HFM cartridge was 0.5 ml/min. This would correspond to a flow rate of 10 ml/min. in a larger pediatric cartridge (e.g. hemofilter from PrismafleX HF20 set, Gambro).

Figure 12:
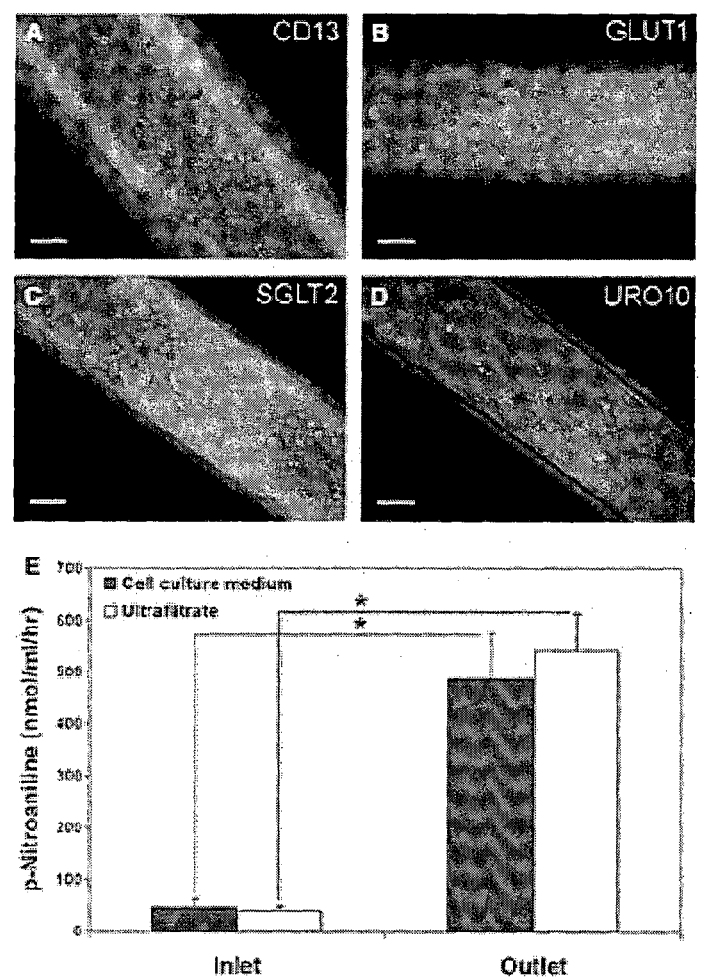
FIG. 12. HPTC performance after perfusion with human hemofiltrate at a relevant flow rate. The extra-HFM space of 25-HFM bioreactors was perfused for 16 hrs with human hemofiltrate at a flow rate of 0.5 ml/min. Panels (A-D) show expression of CD13, GLUT1, SGLT2 and URO10 detected by immunofluorescence (green) in HPTC epithelia on the outer HFM surfaces after the 16-hr perfusion period (cell nuclei: blue). The epithelia remained confluent and displayed a normal morphology. Scale bars: 100 μm. The bars in (E) show the amounts of p-nitroaniline (mean_SD; n=3), which is generated in a reaction catalysed by the brush border enzyme GGT. The amounts of p-nitroaniline were measured at the inlet and outlet ports of the bioreactors. The differences between the mean values (inlet and outlet port) were 10.6-fold when cell culture medium was used and 14.2-fold in the presence of hemofiltrate. The differences in the amounts of p-nitroaniline measured at the inlet and outlet ports under the respective conditions were significant (indicated by asterisks). Perfusion of the bioreactor with hemofiltrate at a flow rate of 0.5 ml/min. (white bars) did not significantly alter the amounts of p-nitroaniline in comparison to perfusion with cell culture medium at a flow rate of 80 μl/min. (black bars).

The results showed that after perfusion with hemofiltrate at 0.5 ml/min a confluent epithelium with a similar morphology and marker expression pattern was present (FIG. 12) as observed during the previous experiments (compare FIG. 14). Furthermore, perfusion with hemofiltrate and higher flow rates did not affect GGT activity (FIG. 12E, see also FIG. 14). Together, the results suggested that a robust and functional epithelium was formed by HPTC on the outer surfaces of unmodified commercial HFM that was not negatively affected by conditions mimicking the situation during large animal experiments and clinical trials.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

As used in this specification and the appended claims, the singular forms "a", "an" and "the" include plural reference unless the context clearly dictates otherwise. As used in this specification and the appended claims, the terms "comprise", "comprising", "comprises" and other forms of these terms are intended in the non-limiting inclusive sense, that is, to include particular recited elements or components without excluding any other element or component. As used in this specification and the appended claims, all ranges or lists as given are intended to convey any intermediate value or range or any sublist contained therein. Unless defined otherwise all technical and scientific terms used herein have the same meaning as commonly understood to one of ordinary skill in the art to which this invention belongs.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

REFERENCES

1. Fissell W H, Dyke D B, Weitzel W F, et al. Bioartificial kidney alters cytokine response and haemodynamics in endotoxin-challenged uremic animals. *Blood Purif* 2002; 20: 55-60.

2. Fissell W H, Lou L, Abrishami S, et al. Bioartificial kidney ameliorates gram-negative bacteria-induced septic shock in uremic animals. *J Am Soc Nephrol.* 2003; 14: 454-61.
3. Humes H D, Buffington D A, MacKay S M, et al. Replacement of renal function in uremic animals with a tissue-engineered kidney. *Nat Biotechnol.* 1999; 17: 451-5.
4. Humes H D, Fissell W H, Weitzel W F, et al. Metabolic replacement of kidney function in uremic animals with a bioartificial kidney containing human cells. *Am J Kidney Dis.* 2002; 39: 1078-87.
5. Mao H, Wang X, Ying X, et al. Effect of continuous bioartificial kidney therapy on porcine multiple organ dysfunction syndrome with acute renal failure. *ASAIO J* 2007; 53: 329-34.
6. Wang H, Zhang M, Wang X, et al. Improvement of cytokine response and survival time by bioartificial kidney therapy in acute uremic pigs with multi-organ dysfunction. *Int J Artif Organs.* 2010; 33: 526-34.
7. Saito A, Sawada K, Fujimura S, et al. Evaluation of bioartificial renal tubule device prepared with lifespan-extended human renal proximal tubular epithelial cells. *Nephrol Dial Transplant.* 2012; 27: 3091-9.
8. Humes H D, Weitzel W F, Bartlett R H, et al. Initial clinical results of the bioartificial kidney containing human cells in ICU patients with acute renal failure. *Kidney Int.* 2004; 66: 1578-88.
9. Tumlin J, Wali R, Williams W, et al. Efficacy and safety of renal tubule cell therapy for acute renal failure. *J Am Soc Nephrol.* 2008; 19: 1034-40.
10. Tasnim F, Deng R, Hu M, et al. Achievements and challenges in bioartificial kidney development. *Fibrogenesis Tissue Repair.* 2010; 3: 14.
11. Chertow G M, Waikar S S. Toward the promise of renal replacement therapy. *J Am Soc Nephrol.* 2008; 19: 839-40.
12. Oo Z Y, Deng R, Hu M, et al. The performance of primary human renal cells in hollow fiber bioreactors for bioartificial kidneys. *Biomaterials.* 2011; 32: 8806-15.
13. Ni M, Teo J C, Ibrahim M S, et al. Characterization of membrane materials and membrane coatings for bioreactor units of bioartificial kidneys. *Biomaterials.* 2011; 32: 1465-76.
14. Ni M, Zimmermann P K, Kandasamy K, et al. The use of a library of industrial materials to determine the nature of substrate dependent performance of primary adherent human cells. *Biomaterials.* 2012; 33: 353-64.
15. Ueda H, Watanabe J, Konno T, et al. Asymmetrically functional surface properties on biocompatible phospholipid polymer membrane for bioartificial kidney. *J Biomed MaterRes A.* 2006; 77: 19-27.
16. Minuth W W, Schumacher K, Strehl R. Renal epithelia in long term gradient culture for biomaterial testing and tissue engineering. *Biomed Mater Eng.* 2005; 15: 51-63.
17. Minuth W W, Strehl R. Technical and theoretical considerations about gradient perfusion culture for epithelia used in tissue engineering, biomaterial testing and pharmaceutical research. *Biomed Mater.* 2007; 2: R1-11.
18. Li Y, Zheng Y, Zhang K, et al. Effects of quantum dots on different renal proximal tubule cell models and on gel-free renal tubules generated in vitro. *Nanotoxicology.* 2012; 6: 121-33.
19. Tasnim F, Kandasamy K, Muck J S, et al. Effects of bone morphogenetic proteins on primary human renal cells and the generation of bone morphogenetic protein-7-expressing cells for application in bioartificial kidneys. *Tissue Eng Part A.* 2012; 18: 262-76.
20. Zhang H, Lau S F, Heng B F, et al. Generation of easily accessible human kidney tubules on two-dimensional surfaces in vitro. *J Cell Mol Med.* 2011; 15: 1287-98.
21. Sanechika N, Sawada K, Usui Y, et al. Development of bioartificial renal tubule devices with lifespan-extended human renal proximal tubular epithelial cells. *Nephrol Dial Transplant.* 2011; 26: 2761-9.
22. Humes H D, MacKay S M, Funke A J, et al. Tissue engineering of a bioartificial renal tubule assist device: in vitro transport and metabolic characteristics. *Kidney Int.* 1999; 55: 2502-14.
23. Fernandez-Real J M, Vayreda M, Richart C, et al. Circulating interleukin 6 levels, blood pressure, and insulin sensitivity in apparently healthy men and women. *J Clin Endocrinol Metab.* 2001; 86: 1154-9.
24. Ozgen N, Terashima M, Aung T, et al. Evaluation of long-term transport ability of a bioartificial renal tubule device using LLC-PK1 cells. *Nephrol Dial Transplant.* 2004; 19: 2198-207.
25. Saito A. Research into the development of a wearable bioartificial kidney with a continuous haemofilter and a bioartificial tubule device using tubular epithelial cells. *Artif Organs.* 2004; 28: 58-63.
26. Saito A, Aung T, Sekiguchi K, et al. Present status and perspective of the development of a bioartificial kidney for chronic renal failure patients. *Ther Apher Dial.* 2006; 10: 342-7.
27. Ip T K, Aebischer P. Renal epithelialcell-controlled solute transport across permeable membranes as the foundation for a bioartificial kidney. *Artif Organs.* 1989; 13: 58-65.
28. Dong X, Chen J, He Q, et al. Construction of bioartificial renal tubule assist device in vitro and its function of transporting sodium and glucose. *J Huazhong Univ Sci Technolog Med Sci.* 2009; 29: 517-21.
29. Tsuruoka S, Nishiki K, Sugimoto K, et al. Specific therapy of digoxin intoxication in dogs by hybrid kidney overexpressing multidrug resistance protein. *Kidney Int.* 2002; 62:1332-7.
30. Tsuruoka S, Sugimoto K I, Ueda K, et al. Removal of digoxin and doxorubicin by multidrug resistance protein-overexpressed cell culture in hollow fiber. *Kidney Int.* 1999; 56: 154-63.
31. Steensberg A, Fischer C P, Keller C, et al. IL-6 enhances plasma I L-Ira, IL-10, and cortisol in humans. *Am J Physiol Endocrinol Metab.* 2003; 285: E433-7.
32. Boswell R N, Yard B A, Schrama E, et al. Interleukin 6 production by human proximal tubular epithelial cells in vitro: analysis of the effects of interleukin-1 alpha (IL-1 alpha) and other cytokines. *Nephrol Dial Transplant.* 1994; 9: 599-606.
33. Aebischer P, et al. Renal epithelial cells grown on semipermeable hollow fibers as a potential haemofiltrate processor. *ASAIO Trans.* 1987; 33: 96-102.
34. Aebischer P, et al. The bioartificial kidney: progress towards an haemofiltration device with renal epithelial cells processing. *Life Support Syst* 1987; 159-168.
35. Ip T K, et al. Cellular control of membrane permeability. Implications for a bioartificial renal tubule. *ASAIO Trans* 1988; 34:351-355.
36. Uludag H, et al. Transport functions in a bioartificial kidney under uremic conditions. *Int J Artif Organs* 1990; 13:93-97.
37. Uludag H, et al. Control of water flux in a bioartificial kidney. *ASAIO Trans* 1989; 35:523-527.

38. Inagaki M, et al. Prevention of LLC-PK(1) cell overgrowth in a bioartificial renal tubule device using a MEK inhibitor, U0126. *J Biotechnol* 2007; 132:57-64.
39. Terashima M, et al. Evaluation of water and electrolyte transport of tubular epithelial cells under osmotic and hydraulic pressure for development of bioartificial tubules. *Artif Organs* 2001; 25:209-212.
40. Saito, A et al. Present status and perspectives of bioartificial kidneys. *J Artif Organs* 2006; 9:130-135.
41. Saito, A et al. Present status and future perspectives on the development of bioartificial kidneys for the treatment of acute and chronic renal failure patients. *Hemaodial Int* 2011; 15:183-192.
42. Tsuruoka S, et al. Removal of digoxin and doxorubicin by multidrug resistance protein-overexpressed cell culture in hollow fiber. *Kidney Int* 1999; 56:154-163.

What is claimed is:

1. A bioreactor device comprising:
   a housing having a blood inlet port; a blood outlet port; an hemofiltrate inlet port; and an hemofiltrate outlet port;
   one or more porous hollow fiber membranes contained within said housing, each of said one or more hollow fiber membranes being in fluid communication with said blood inlet port and said blood outlet port, and each of said one or more hollow fiber membranes comprising a hemocompatible luminal surface and a cytocompatible exterior surface that is cytocompatible for human primary renal proximal tubule cells (HPTCs) or stem cell-derived HPTC-like cells,
   each of said cytocompatible exterior surfaces covered with a confluent layer of said HPTCs or stem cell-derived HPTC-like cells, and being in fluid communication with said hemofiltrate inlet port and said hemofiltrate outlet port.

2. The bioreactor device according to claim 1, wherein the confluent layer of HPTCs or stem-cell derived HPTC-like cells comprises a differentiated single layer epithelium in which the paracellular spaces are sealed by tight junctions.

3. The bioreactor device according to claim 1, wherein the HPTCs or stem-cell derived HPTC-like cells are grown directly onto each of said cytocompatible exterior surfaces, each of said cytocompatible exterior surfaces being free from an additional coating.

4. The bioreactor device according to claim 1, wherein each of said cytocompatible exterior surfaces has a rough texture relative to the hemocompatible luminal surface.

5. The bioreactor device according to claim 1, wherein each of said cytocompatible exterior surfaces is non-hemocompatible.

6. The bioreactor device according to claim 1, wherein each of said cytocompatible exterior surfaces has large pores relative to pores on the hemocompatible luminal surface.

7. The bioreactor device according to claim 6, wherein said large pores are in the micrometer range.

8. The bioreactor device according to claim 1, wherein said hemocompatible luminal surface has pores sized to allow for rapid fluid exchange but sized to exclude serum albumin.

9. The bioreactor device according claim 8, wherein said pores on the hemocompatible luminal surface are in the sub-micron range.

10. The bioreactor device according to claim 1, wherein said hemocompatible luminal surface comprises a smooth surface.

11. The bioreactor device according to claim 1, wherein said cytocompatible exterior surface comprises one or more of polysulfone, polyethersulfone, polyarylethersulfone, polycarbonate, polyacrylonitrile, polyethylene, polyolefin, polypropylene and polyviylidene fluoride, ethylene vinyl alcohol copolymer, polymethylmethacrylate, polyamide and polyacrylate, optionally blended with a hydrophilic polymer such as polyviylpyrrolidone or polyurethane.

12. The bioreactor device according to claim 1, comprising at least two of said hollow fiber membranes that are packed in the bioreactor device at a density less than the density of hollow fiber membranes in a Gambro PrismafleX HF20 polyarylethersulfone hemodialysis cartridge or a Fresenius HF80S polysulfone hemodialysis cartridge.

13. A bioartificial kidney device comprising:
   a hemofiltration device, said hemofiltration device comprising:
      a housing with a blood inlet port and a blood outlet port;
      one or more semi-permeable hollow fiber membranes contained within said housing, each of said one or more hollow fiber membranes being in fluid communication with said blood inlet port and said blood outlet port, and each of said one or more hollow fiber membranes comprising a hemocompatible luminal surface and an exterior surface,
      each of said exterior surfaces being in fluid communication with an hemofiltrate outlet port; and
   a bioreactor device comprising:
      a housing having a blood inlet port; a blood outlet port; an hemofiltrate inlet port; and an hemofiltrate outlet port;
      one or more porous hollow fiber membranes contained within said housing, each of said one or more hollow fiber membranes being in fluid communication with said blood inlet port and said blood outlet port, and each of said one or more hollow fiber membranes comprising a hemocompatible luminal surface and a cytocompatible exterior surface that is cytocompatible for human primary renal proximal tubule cells (HPTCs) or stem cell-derived HPTC-like cells,
      each of said cytocompatible exterior surfaces covered with a confluent layer of said HPTCs or stem cell-derived HPTC-like cells, and being in fluid communication with said hemofiltrate inlet port and said hemofiltrate outlet port, wherein said blood inlet port of said bioreactor device being in fluid connection with said blood outlet port of said hemofiltration device, and said hemofiltrate inlet port of said bioreactor being in fluid communication with said hemofiltrate outlet port of said hemofiltration device.

14. The bioartificial kidney device according to claim 13, further comprising:
   a first fluid line for connecting to a bloodstream of a subject, said first fluid line being in fluid communication with said blood inlet port of said hemofiltration device;
   a first pump for controlling blood flow rate from said subject;
   a first reservoir for holding hemofiltrate, said first reservoir in fluid communication with said hemofiltrate outlet port of said hemofiltration device and in fluid communication with said hemofiltrate inlet port of said bioreactor device;
   a second pump for controlling flow rate from said first reservoir,
   a second fluid line in fluid communication with said blood outlet port of said hemofiltration device and in fluid communication with said blood inlet port of said bioreactor device;

a third fluid line in fluid communication with said second fluid line and in fluid communication with said subject, said third fluid line connected to said second fluid line at a branch point;

a three way connector at said branch point for controlling the amount of blood flowing from said blood outlet port of said hemofiltration device to said blood inlet port of said bioreactor device and for optionally diverting at least a portion of said blood into said third fluid line;

a fourth fluid line in fluid communication with said blood outlet port of said bioreactor device and in fluid communication with said third fluid line;

a third pump for controlling blood flow into said blood inlet port of said bioreactor device;

a second reservoir for holding replacement fluid, said second reservoir being in fluid communication either with said blood inlet port of said hemofiltration device or with said third fluid line;

a fourth pump for controlling flow rate from said second reservoir; and optionally a fifth pump for controlling blood flow rate from said third line into said subject.

15. The bioartificial kidney device according to claim 14, further comprising a third reservoir for collecting waste from said bioreactor device, said third reservoir in fluid communication with said hemofiltrate outlet port of said bioreactor device.

16. The bioartificial kidney device according to claim 15, wherein said third reservoir is also in fluid communication with said first reservoir, said bioartificial kidney device further comprising a sixth pump for controlling flow rate from said third reservoir to said first reservoir.

17. A method of providing renal function to a subject comprising:

connecting a bioartificial kidney device to a subject in need of renal replacement therapy, wherein the bioartificial kidney device comprises:

a hemofiltration device, said hemofiltration device comprising:

a housing with a blood inlet port and a blood outlet port;

one or more semi-permeable hollow fiber membranes contained within said housing, each of said one or more hollow fiber membranes being in fluid communication with said blood inlet port and said blood outlet port, and each of said one or more hollow fiber membranes comprising a hemocompatible luminal surface and an exterior surface, each of said exterior surfaces being in fluid communication with an hemofiltrate outlet port; and a bioreactor device comprising:

a housing having a blood inlet port; a blood outlet port; an hemofiltrate inlet port; and an hemofiltrate outlet port;

one or more porous hollow fiber membranes contained within said housing, each of said one or more hollow fiber membranes being in fluid communication with said blood inlet port and said blood outlet port, and each of said one or more hollow fiber membranes comprising a hemocompatible luminal surface and a cytocompatible exterior surface that is cytocompatible for human primary renal proximal tubule cells (HPTCs) or stem cell-derived HPTC-like cells, each of said cytocompatible exterior surfaces covered with a confluent layer of said HPTCs or stem cell-derived HPTC-like cells, and being in fluid communication with said hemofiltrate inlet port and said hemofiltrate outlet port, wherein said blood inlet port of said bioreactor device being in fluid connection with said blood outlet port of said hemofiltration device, and said hemofiltrate inlet port of said bioreactor being in fluid communication with said hemofiltrate outlet port of said hemofiltration device.

18. The method according to claim 17, wherein the method provides blood hemofiltration to the subject.

19. The method according to claim 17, wherein said connecting comprises connecting the bioartificial kidney device to the subject via said first fluid line and said third fluid line so that blood flows from said subject into said first fluid line, through said bioartificial kidney device and into said subject via said third fluid line, wherein the bioartificial kidney device further comprises:

a first fluid line for connecting to a bloodstream of a subject, said first fluid line being in fluid communication with said blood inlet port of said hemofiltration device;

a first pump for controlling blood flow rate from said subject;

a first reservoir for holding hemofiltrate, said first reservoir in fluid communication with said hemofiltrate outlet port of said hemofiltration device and in fluid communication with said hemofiltrate inlet port of said bioreactor device;

a second pump for controlling flow rate from said first reservoir, a second fluid line in fluid communication with said blood outlet port of said hemofiltration device and in fluid communication with said blood inlet port of said bioreactor device;

a third fluid line in fluid communication with said second fluid line and in fluid communication with said subject, said third fluid line connected to said second fluid line at a branch point;

a three way connector at said branch point for controlling the amount of blood flowing from said blood outlet port of said hemofiltration device to said blood inlet port of said bioreactor device and for optionally diverting at least a portion of said blood into said third fluid line;

a fourth fluid line in fluid communication with said blood outlet port of said bioreactor device and in fluid communication with said third fluid line;

a third pump for controlling blood flow into said blood inlet port of said bioreactor device;

a second reservoir for holding replacement fluid, said second reservoir being in fluid communication either with said blood inlet port of said hemofiltration device or with said third fluid line;

a fourth pump for controlling flow rate from said second reservoir; and optionally a fifth pump for controlling blood flow rate from said third line into said subject.

20. The method according to claim 17, wherein said first pump controls blood flow from said subject into said blood inlet port of said hemofiltration device at a flow rate of from about 100 ml/min to about 200 ml/min; and/or said second pump controls hemofiltrate flow from the first reservoir into said hemofiltrate inlet port of said bioreactor device at a flow rate of from about 10 ml/min to about 100 ml/min; and/or said third pump controls blood flow into said blood inlet port of said bioreactor device at a flow rate of from about 10 ml/min to about 100 ml/min.

\* \* \* \* \*